United States Patent
Olson et al.

(10) Patent No.: US 12,029,718 B2
(45) Date of Patent: Jul. 9, 2024

(54) PROCESS FOR PRODUCTION OF ESSENTIALLY PURE DELTA-9-TETRAHYDROCANNABINOL

(71) Applicant: CCT SCIENCES, LLC, Clearwater, FL (US)

(72) Inventors: Kyle Olson, Clearwater, FL (US); Harold Meckler, Delmar, NY (US); Marcus Brackeen, Research Triangle Park, NC (US); Mario Tremblay, Clearwater, FL (US)

(73) Assignee: CCT SCIENCES, LLC, Clearwater, FL (US)

( * ) Notice: Subject to any disclaimer, the term of this patent is extended or adjusted under 35 U.S.C. 154(b) by 0 days.

(21) Appl. No.: 17/522,866

(22) Filed: Nov. 9, 2021

(65) Prior Publication Data

US 2023/0149342 A1    May 18, 2023

(51) Int. Cl.
| | | |
|---|---|---|
| *A23L 33/105* | (2016.01) | |
| *A61K 31/05* | (2006.01) | |
| *A61K 31/352* | (2006.01) | |
| *B01D 1/08* | (2006.01) | |
| *B01D 3/10* | (2006.01) | |
| *B01D 3/14* | (2006.01) | |
| *B01D 11/04* | (2006.01) | |
| *B01D 39/20* | (2006.01) | |
| *B01J 31/14* | (2006.01) | |
| *C07C 37/74* | (2006.01) | |
| *C07D 311/78* | (2006.01) | |
| *B01D 11/00* | (2006.01) | |
| *B01D 15/08* | (2006.01) | |

(52) U.S. Cl.
CPC .......... *A61K 31/352* (2013.01); *A23L 33/105* (2016.08); *A61K 31/05* (2013.01); *B01D 1/08* (2013.01); *B01D 3/10* (2013.01); *B01D 3/143* (2013.01); *B01D 11/0492* (2013.01); *B01D 39/2068* (2013.01); *B01J 31/143* (2013.01); *C07C 37/74* (2013.01); *C07D 311/78* (2013.01); *A23V 2002/00* (2013.01); *A61K 2236/55* (2013.01); *B01D 2011/002* (2013.01); *B01D 15/08* (2013.01)

(58) Field of Classification Search
CPC ................................ A23L 33/105; B01D 3/10
See application file for complete search history.

(56) References Cited

U.S. PATENT DOCUMENTS

| | | |
|---|---|---|
| 2,304,559 A | 12/1942 | Adams |
| 2,419,935 A | 5/1947 | Adams |
| 2,419,936 A | 5/1947 | Adams |
| 2,509,387 A | 5/1950 | Adams |
| 3,734,930 A | 5/1973 | Razdan |
| 3,920,705 A | 11/1975 | Petrzilka |
| 4,025,516 A | 5/1977 | Razdan et al. |
| 4,054,582 A | 10/1977 | Blanchard et al. |
| 4,075,230 A | 2/1978 | Archer et al. |
| 4,102,902 A | 7/1978 | Archer et al. |
| 4,116,979 A | 9/1978 | Razdan et al. |
| 4,131,614 A | 12/1978 | Ryan |
| 4,148,809 A | 4/1979 | Day et al. |
| 4,171,315 A | 10/1979 | Ryan |

(Continued)

FOREIGN PATENT DOCUMENTS

| | | |
|---|---|---|
| WO | WO1994014790 A1 | 7/1994 |
| WO | WO1995020958 A1 | 8/1995 |

(Continued)

OTHER PUBLICATIONS

Nov. 4, 2019, AAPS PharmSci 360, Novel Authentication Technology Using Molecular Tags as PCID in Solid Oral Dosage Forms.
Nov. 28, 2020, Precision Extraction Solutions, Cannabis Distillation/ Short Path vs Wiped Film.
Nov. 29, 2020, Royal CBD, Full Spectrum vs Broad Spectrum vs CBD Isolate: Difference Explained.
Nov. 29, 2020, Greenstate, Why do I feel high on CBD? 4 Reasons and what to do about it.

(Continued)

*Primary Examiner* — John S Kenyon
(74) *Attorney, Agent, or Firm* — JUNEAU & MITCHELL; Todd L. Juneau

(57) ABSTRACT

The present invention describes a method which outlines a process for conversion of CBD to a $\Delta^9$-tetrahydrocannabinol ($\Delta^9$-THC) compound or derivative thereof involving treating a naturally produced CBD intermediate compound with an organoaluminum-based Lewis acid catalyst, under conditions effective to produce the $\Delta^9$-tetrahydrocannabinol compound or derivative thereof at a relatively high concentration. The source of the CBD is from industrial hemp having less than 0.3% $\Delta^9$-THC and extracting and purifying a CBD distillate or isolate or a combination thereof. This procedure will produce $\Delta^9$-THC that is essentially free from any other cannabinoids other than some trace amounts of the initial CBD starting material, or about 95% $\Delta^9$-THC and 2-4% CBD. Another aspect of the present invention relates to a process for further purification and enrichment of the $\Delta^9$-THC using distillation and collecting an essentially pure fraction of $\Delta^9$-THC using additional distillation or enrichment form of purification. Included are methods and processes to scale the reaction from the lab to large scale manufacturing. Included are methods for adding a molecule marker to authenticate high purity $\Delta^9$-THC products. Formulations and uses for pharmaceuticals, nutraceuticals, food products, and topicals are also provided.

32 Claims, 9 Drawing Sheets

(56) References Cited

U.S. PATENT DOCUMENTS

| | | | |
|---|---|---|---|
| 4,179,517 | A | 12/1979 | Mechoulam et al. |
| 4,433,183 | A | 2/1984 | Fehr et al. |
| 4,876,276 | A | 10/1989 | Mechoulam et al. |
| 4,933,363 | A | 6/1990 | Elsohly |
| 5,227,537 | A | 7/1993 | Stoss et al. |
| 5,292,899 | A | 3/1994 | Tius et al. |
| 5,338,753 | A | 8/1994 | Burstein |
| 5,389,375 | A | 2/1995 | ElSohly |
| 5,440,052 | A | 8/1995 | Makriyannis et al. |
| 5,538,993 | A | 7/1996 | Mechoulam et al. |
| 5,605,928 | A | 2/1997 | Mechoulam et al. |
| 5,635,530 | A | 6/1997 | Mechoulam et al. |
| 5,932,610 | A | 8/1999 | Shohami et al. |
| 6,008,383 | A | 12/1999 | Elsohly et al. |
| 6,162,829 | A | 12/2000 | Burstein |
| 6,274,635 | B1 | 8/2001 | Travis |
| 6,563,009 | B1 | 5/2003 | Kunos et al. |
| 6,610,737 | B1 | 8/2003 | Garzon et al. |
| 6,630,507 | B1 | 10/2003 | Hampson et al. |
| 6,689,881 | B1 | 2/2004 | Bernardelli |
| 6,730,519 | B2 | 5/2004 | Elsohly et al. |
| 6,946,150 | B2 | 9/2005 | Whittle |
| 6,949,582 | B1 | 9/2005 | Wallace |
| 7,399,872 | B2 | 7/2008 | Webster et al. |
| 7,674,922 | B2 | 3/2010 | Burdick et al. |
| 8,106,244 | B2 | 1/2012 | Burdick et al. |
| 10,624,872 | B1 | 4/2020 | McCorkle et al. |
| 10,849,876 | B2 | 12/2020 | McCorkle et al. |
| 10,980,773 | B2 | 4/2021 | McCorkle et al. |
| 2002/0111377 | A1 | 8/2002 | Stinchcomb |
| 2003/0017216 | A1 | 1/2003 | Schmidt |
| 2004/0043946 | A1 | 3/2004 | Popp |
| 2004/0054007 | A1 | 3/2004 | Burstein |
| 2004/0110827 | A1 | 6/2004 | Aviv |
| 2004/0225011 | A1 | 11/2004 | Burstein |
| 2004/0242593 | A1 | 12/2004 | Moore |
| 2004/0248970 | A1 | 12/2004 | Webster |
| 2004/0249174 | A1 | 12/2004 | Silverberg |
| 2005/0032881 | A1 | 2/2005 | Garzon |
| 2005/0049298 | A1 | 3/2005 | Goodwin |
| 2010/0069651 | A1 | 3/2010 | Burdick et al. |
| 2010/0210860 | A1 | 8/2010 | Erler et al. |

FOREIGN PATENT DOCUMENTS

| | | | | |
|---|---|---|---|---|
| WO | WO2001013886 | A1 | 3/2001 | |
| WO | WO2001095899 | A2 | 12/2001 | |
| WO | WO2002032420 | A1 | 4/2002 | |
| WO | WO2002070506 | A2 | 9/2002 | |
| WO | WO2002089945 | A2 | 11/2002 | |
| WO | WO2003091189 | A1 | 11/2003 | |
| WO | WO2004026857 | A2 | 4/2004 | |
| WO | WO2004092101 | A2 | 10/2004 | |
| WO | WO2005100333 | A1 | 10/2005 | |
| WO | WO2005120478 | A1 | 12/2005 | |
| WO | WO20060074252 | A1 | 1/2006 | |
| WO | WO2006053766 | A1 | 5/2006 | |
| WO | WO2016153347 | A1 | 9/2016 | |
| WO | WO-2016153347 | A1 * | 9/2016 | ........... C07C 37/004 |
| WO | WO-2019060986 | A1 * | 4/2019 | ......... B01D 11/0284 |
| WO | WO2020198876 | A1 | 10/2020 | |

OTHER PUBLICATIONS

Aug. 20, 2021, Fieser & Fieser, Reagents for Organic Synthesis.

Sep. 7, 2021, PubChem, delta9-Tetrahydrocannabinol.

Aug. 17, 2020, Journal of Medicinal Chemistry, The Essential Medicinal Chemistry of Cannabidiol (CBD).

* cited by examiner

FIGURE 2 - Process

FIGURE 6

(i) verifying a source of industrial hemp as having <0.3% Δ9-THC by HPLC;
(ii) extracting a cannabidiol extract from industrial hemp having less than 0.3% Δ9-THC, dissolving the extract in a solvent, and reacting with an organoaluminum catalyst in hexane in an inert atmosphere under ambient temperature;

(iii) stirring the for 6-20 hours at -20-100 ° C, quenching with water or alcohol, and filtering and rinsing the reaction mixture using dichloromethane, hexanes, or a combination;

(iv) Vacuum distilling the crude Δ9-THC oil with a short path vacuum distillation system until a clear Δ9-THC distillate starts to condense and then immediately stopping the vacuum distilling, wherein said vacuum distilling removes residual solvent and volatile cannabidiol impurities from the clear Δ9-THC distillate; and (v) Wiped film distilling the clear Δ9-THC distillate with a wiped film distillation unit to obtain a Δ9-THC oil having >90-99% Δ9-THC by HPLC, wherein said wiped film distilling removes high temperature cannabinoid impurities having a non-vacuum boiling higher than 180°C;

(vi) verifying purity of >90-99% Δ9-THC using a verification method selected from the group consisting of post decarboxylation, HPLC, GC, GC-MS, GC-FID, HPLC-MS, HPLC-UV, HPLC-DAD, HPLC-ESI-qTOF, HPLC-MS/MS, UPLC, UPLC-qTOF, MALDI-MS, TLC, FTIR, and NMR.

FIGURE 7

(i) extracting a cannabidiol extract from industrial hemp having less than 0.3% Δ9-THC, dissolving the extract in a solvent, reacting with an organoaluminum catalyst in an inert atmosphere, quenching and filtering the reaction mixture;

(ii) performing short path vacuum distillation followed by wiped film distillation to obtain a Δ9-THC oil comprising 93% Δ9-THC and 4% unreacted CBD by HPLC.

(iii) adding a signature marker such as a rt-PCR detectable DNA or a specific combination of inactive ingredients to a product or package containing the high purity Δ9-THC oil for authentication and identification and to detect counterfeit products.

ion of highly pure $\Delta^9$-tetrahydrocannabinol (also
PROCESS FOR PRODUCTION OF ESSENTIALLY PURE DELTA-9-TETRAHYDROCANNABINOL

FIELD OF THE INVENTION

The present invention relates to an industrial scale process for preparation of highly pure $\Delta^9$-tetrahydrocannabinol (also referred to as $\Delta^9$-THC, or delta-9-tetrahydrocannabinol), intermediate compounds thereof, and derivative compounds thereof, from a starting material that is an extract of industrial hemp having 0.3% or less $\Delta^9$-THC, subjecting the extract to specific reaction temperatures, pressures, duration, and solvents, in the presence of an organoaluminum catalyst, to isomerize cannabidiol (CBD) into $\Delta^9$-THC, and using a split path distillation process to obtain a highly pure $\Delta^9$-THC oil. Purity is 90-99% of the presence of $\Delta^9$-THC on a weight to weight basis as detected by HPLC, and is useful for pharmaceutical, nutraceutical, skin care and/or cosmetic compositions. Additionally, the method maintains as an intentional impurity a residual CBD stabilizing composition with the starting material to stabilize the $\Delta^9$-THC isomer.

BACKGROUND OF THE INVENTION

Hemp is a variety of the *Cannabis sativa* plant species that is grown specifically for its derived products. Some hemp varieties are cultivated for industrial uses such as textiles, rope and paper where others have high levels of beneficial nutraceutical cannabinoids. One of the most popular of these compounds is cannabidiol (CBD), which has been used in a variety of consumer products in recent years. For industrial hemp to be federally legal it must contain less than 0.3% of $\Delta^9$-THC on dry weight basis. The current genetics in the space have allowed for the cultivation of high CBD strains with less than 0.3% $\Delta^9$-THC with relative ease, which has opened this crop to a very large nationwide market.

However, obtaining $\Delta^9$-THC from CBD typically is accompanied by $\Delta^8$-tetrahydrocannabinol ($\Delta^8$-THC) formation due to it being the more thermodynamically stable isomer of the two. It is also difficult or impossible to generate high purity, such as greater than 90%, of the $\Delta^9$-THC without extensive steps of separation and purification. Previously, $\Delta^9$-THC was derived from synthetic starting material, and not from natural CBD distillate and/or CBD isolate.

Accordingly, there is a need for improved methods for obtaining highly pure $\Delta^9$-THC from industrial hemp having 0.3% or less THC.

SUMMARY OF THE INVENTION

The present invention is directed to a process for the preparation of high purity $\Delta^9$-THC from CBD, wherein the purity is greater than 90%-95% $\Delta^9$-THC, without any significant formation of other cannabinoids, including $\Delta^8$-THC or the other isomers of THC. The only measurable cannabinoid in this invention, other than the $\Delta^9$-THC, consists of unreacted CBD. Most importantly, this invention is based on using CBD that is extracted from hemp that contained 0.3% or less $\Delta^9$-THC both in the original hemp and 0.3% or less $\Delta^8$-THC in the CBD isolate was used to derive the high purity $\Delta^9$-THC.

In a preferred non-limiting embodiment, the invention includes a process for the preparation of a high purity $\Delta^9$-tetrahydrocannabinol ($\Delta^9$-THC) oil from CBD that avoids traditional crystallization, isolation, and filtering steps.

The inventive process starts with an industrial hemp plant that is less than 0.3% $\Delta^9$-THC and using extraction and purification techniques to derive a cannabidiol (CBD) distillate or isolate. The next steps comprise: dissolving the CBD distillate or isolate in dichloromethane to create a homogenized mixture; adding the homogenized mixture to a reactor vessel continuously purged with an inert gas and adding a 10 mol % solution of organoaluminum catalyst in hexane slowly over 30 minutes at a temperature of 18-26° C. to create a reaction mixture; stirring the reaction mixture for approximately 6-20 hours at a temperature of −20° C. to about 70° C.; quenching the reaction mixture with water or a $C_2$-$C_4$ alcohol, and stirring for 1 hour; filtering the reaction mixture through a filter of diatomaceous earth, perlite, or cellulose to collect a filtrate, and rinsing the filter and reaction vessel with a rinse solvent selected from dichloromethane, hexanes, or a combination of both, and combining the filtrate and the rinse solvent to obtain a combined filtrate and rinse; and performing a split path distillation of the combined filtrate and rinse, wherein the split path distillation comprises a short path distillation and a wiped film distillation to remove terpenes, high volatiles, or high boiling point cannabinoids from the combined filtrate and rinse, to obtain a $\Delta^9$-THC oil comprising about 93% or greater $\Delta^9$-THC and trace amounts of about 4% CBD.

The invention includes a process for adding a signature marker molecule to authenticate the product and deter counterfeit products.

The invention also includes a method of administering the $\Delta^9$-THC oil provided by the process herein to a patient in need thereof, comprising formulating the $\Delta^9$-THC oil as an oral or topical composition, and delivering the oral or topical composition to a patient in need thereof, wherein the patient has nausea, anxiety, stress, chronic pain, acute pain, opioid withdrawal, narcotic relapse risk, or requires an appetite stimulant.

BRIEF DESCRIPTION OF THE FIGURES

FIG. 6 is a process flowchart showing another preferred embodiment of the inventive process described and claimed herein for: (i) verifying a source of industrial hemp as having <0.3% $\Delta^9$-THC by HPLC; (ii) extracting a cannabidiol extract from industrial hemp having less than 0.3% $\Delta^9$-THC, dissolving the extract in a solvent, and reacting with an organoaluminum catalyst in hexane in an inert atmosphere under ambient temperature; (iii) stirring the for 6-20 hours at −20° C. to 70° C., quenching with water or alcohol, and filtering and rinsing the reaction mixture using dichloromethane, hexanes, or a combination; (iv) Vacuum distilling at 15-20 mTorr the crude $\Delta^9$-THC oil with a short path vacuum distillation system until a clear $\Delta^9$-THC distillate starts to condense and then immediately stopping the vacuum distilling, wherein said vacuum distilling removes residual solvent and volatile cannabidiol impurities from the clear $\Delta^9$-THC distillate; and (v) Wiped film distilling the clear $\Delta^9$-THC distillate with a wiped film distillation unit to obtain a $\Delta^9$-THC oil having >90-99% $\Delta^9$-THC by HPLC, wherein said wiped film distilling removes high temperature cannabinoid impurities having a non-vacuum boiling higher than 180° C.; (vi) verifying purity of >90-99% $\Delta^9$-THC using a verification method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), ultra-performance liquid chromatography (UHPLC), thin layer chromatography (TLC), Fourier transform infrared spectroscopy (FTIR), and nuclear magnetic resonance spectrometry (NMR), UV Spectroscopy.

FIG. 7 is a flow chart showing another preferred embodiment of the inventive process described and claimed herein for adding a signature marker molecule to a product containing the $\Delta^9$-THC oil having >90-99% $\Delta^9$-THC made by the process herein.

FIG. 8 shows an example of a rt-PCR graph, where the resulting cycle threshold (Cq) can be compared against negative and positive controls, as shown.

DETAILED DESCRIPTION OF THE INVENTION

Figure 1:
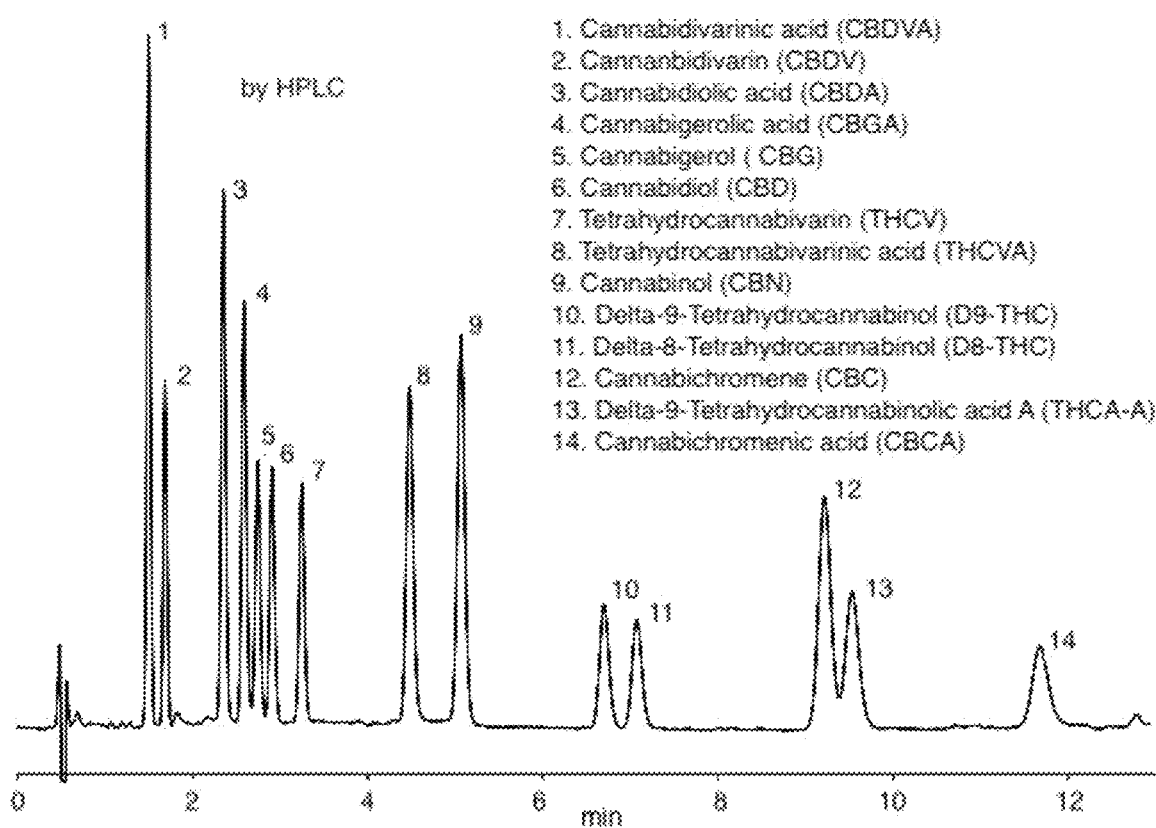
FIG. 1 is an HPLC graph showing the peaks of various cannabinoids.
Figure 2:
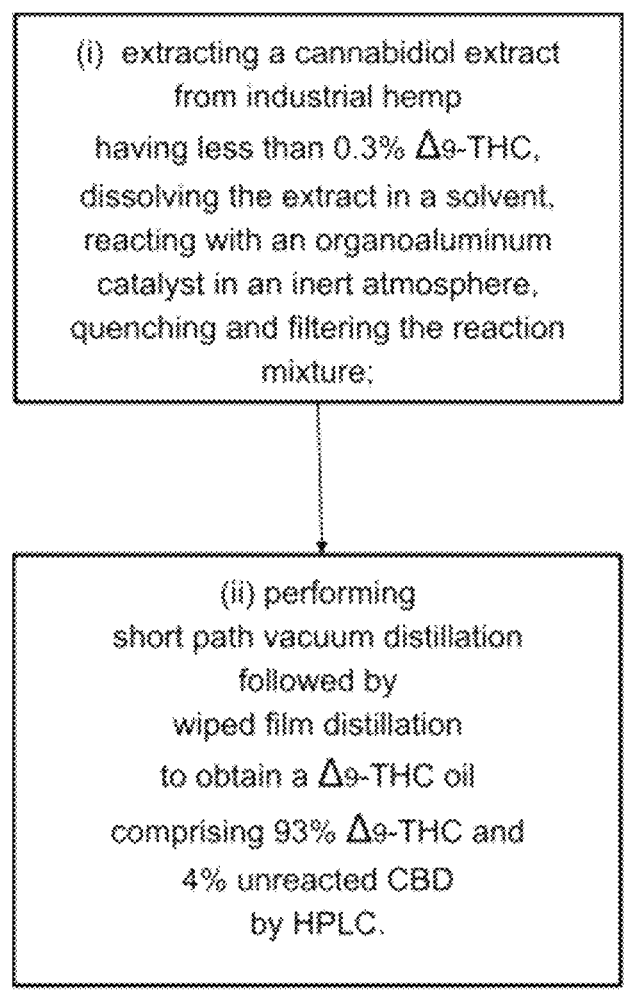
FIG. 2 is a process flowchart showing one preferred embodiment of the inventive process described and claimed herein for (i) extracting a cannabidiol extract from industrial hemp having less than 0.3% $\Delta^9$-THC, dissolving the extract in a solvent, reacting with an organoaluminum catalyst in an inert atmosphere, quenching and filtering the reaction mixture; (ii) performing short path vacuum distillation followed by wiped film distillation to obtain a $\Delta^9$-THC oil comprising about 93% $\Delta^9$-THC and about 4% unreacted CBD by HPLC.
Figure 3:
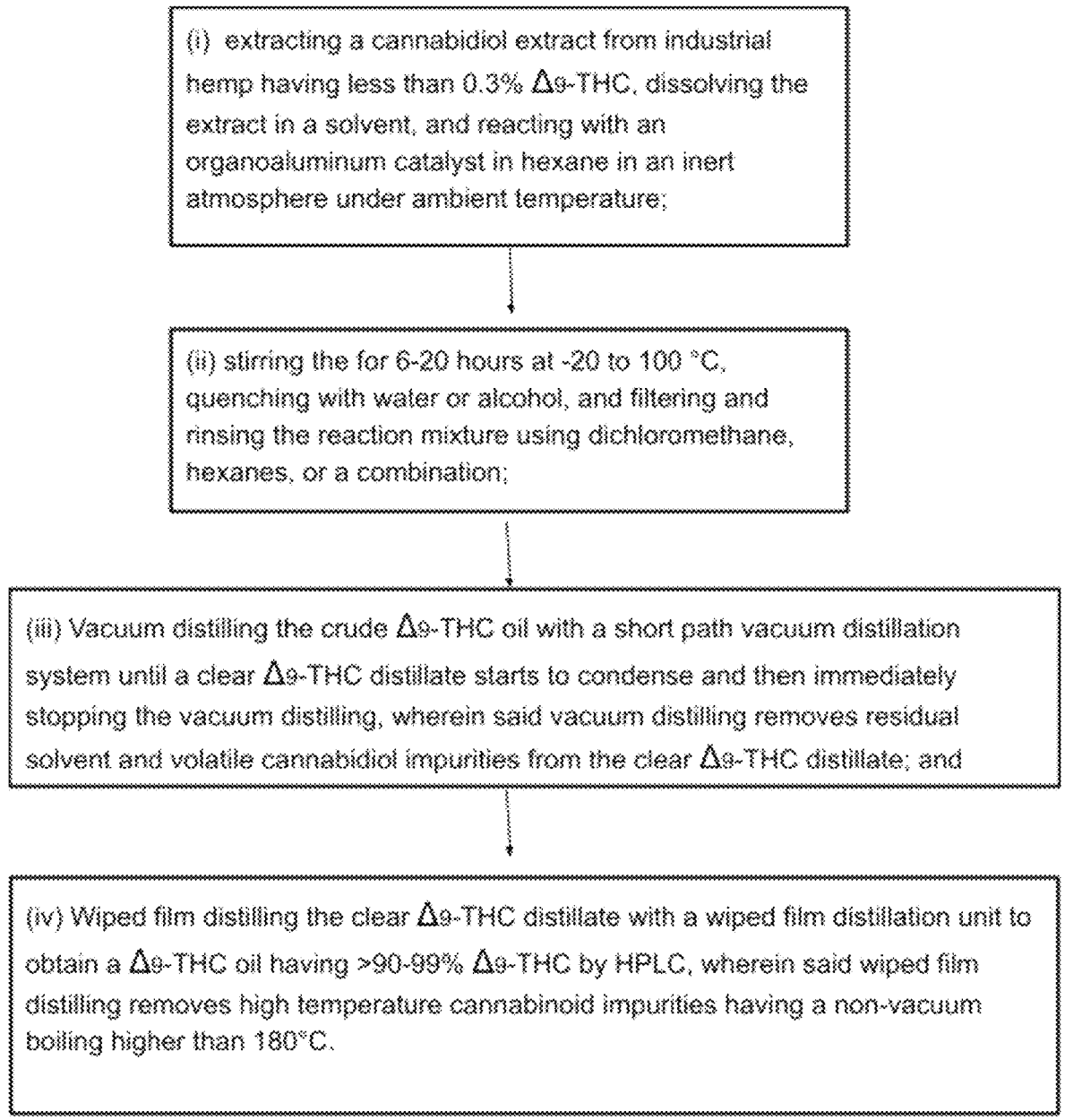
FIG. 3 is a process flowchart showing another preferred embodiment of the inventive process described and claimed herein for (i) extracting a cannabidiol extract from industrial hemp having less than 0.3% $\Delta^9$-THC, dissolving the extract in a solvent, and reacting with an organoaluminum catalyst in hexane in an inert atmosphere under ambient temperature, (ii) stirring the for 6-20 hours at −20° C. to 70° C., quenching with water or alcohol, and filtering and rinsing the reaction mixture using dichloromethane, hexanes, or a combination; (iii) Vacuum distilling the crude $\Delta^9$-THC oil with a short path vacuum distillation system at 15-20 mTorr until a clear $\Delta^9$-THC distillate starts to condense and then immediately stopping the vacuum distilling, wherein said vacuum distilling removes residual solvent and volatile cannabidiol impurities (low boilers) from the clear $\Delta^9$-THC distillate; and (iv) Wiped film distilling the clear $\Delta^9$-THC distillate with a wiped film distillation unit to obtain a $\Delta^9$-THC oil having >90 or 98-99% $\Delta^9$-THC by HPLC, wherein said wiped film distilling separates the desired product from the high temperature cannabinoid impurities having a non-vacuum boiling higher than 180° C.
Figure 4:
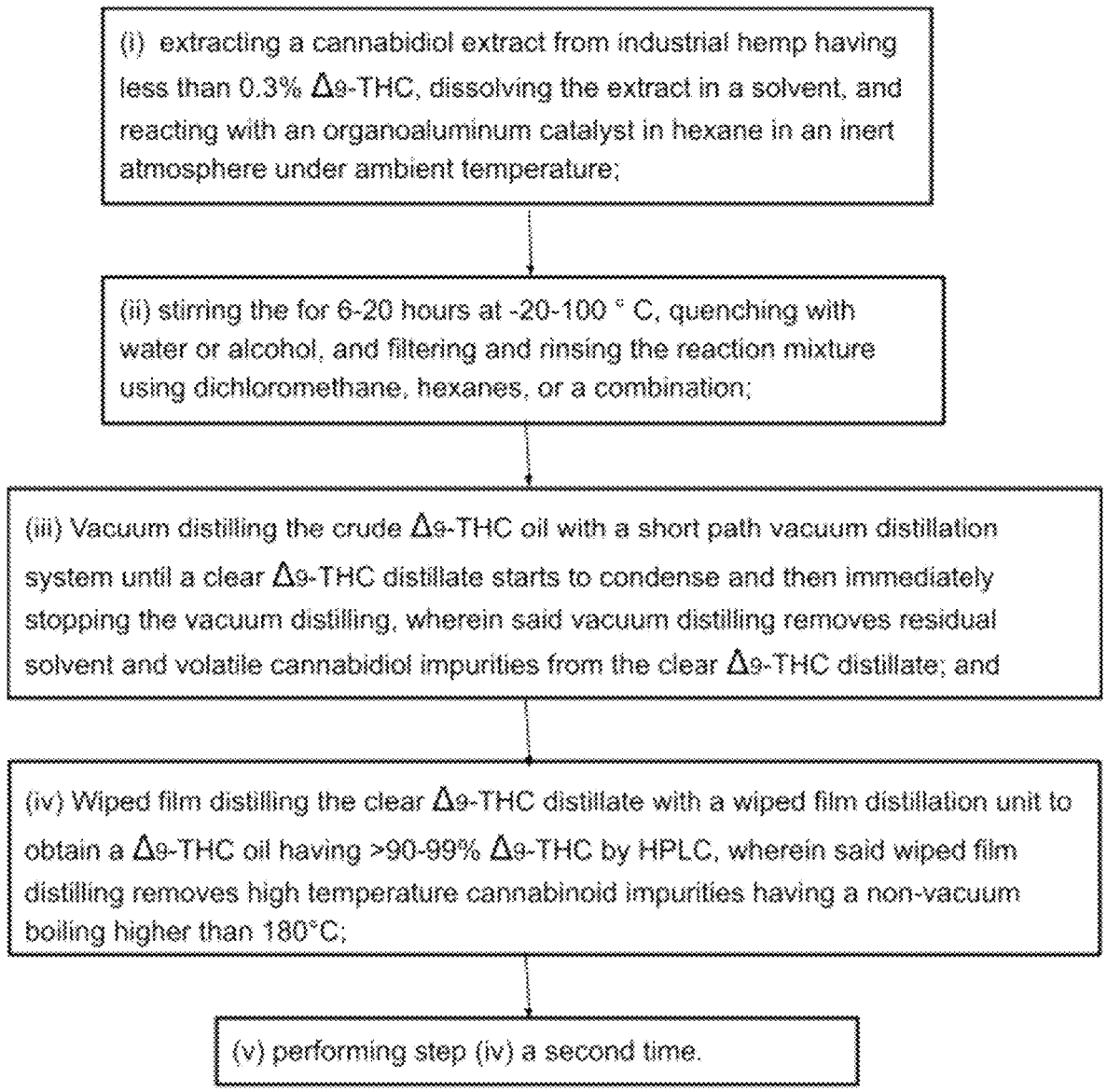
FIG. 4 is a process flowchart showing another preferred embodiment of the inventive process described and claimed herein for (i) extracting a cannabidiol extract from industrial hemp having less than 0.3% $\Delta^9$-THC, dissolving the extract in a solvent, and reacting with an organoaluminum catalyst in hexane in an inert atmosphere under ambient temperature; (ii) stirring the for 6-20 hours at −20° C. to 70° C., quenching with water or alcohol, and filtering and rinsing the reaction mixture using dichloromethane, hexanes, or a combination; (iii) Vacuum distilling the crude $\Delta^9$-THC oil with a short path vacuum distillation system at 15-20 mTorr until a clear $\Delta^9$-THC distillate starts to condense and then immediately stopping the vacuum distilling, wherein said vacuum distilling removes residual solvent and volatile cannabidiol impurities from the clear $\Delta^9$-THC distillate; and (iv) Wiped film distilling the clear $\Delta^9$-THC distillate with a wiped film distillation unit to obtain a $\Delta^9$-THC oil having >90-99% $\Delta^9$-THC by HPLC, wherein said wiped film distilling removes high temperature cannabinoid impurities having a non-vacuum boiling higher than 180° C.; (v) performing step (iv) a second time.
Figure 5:
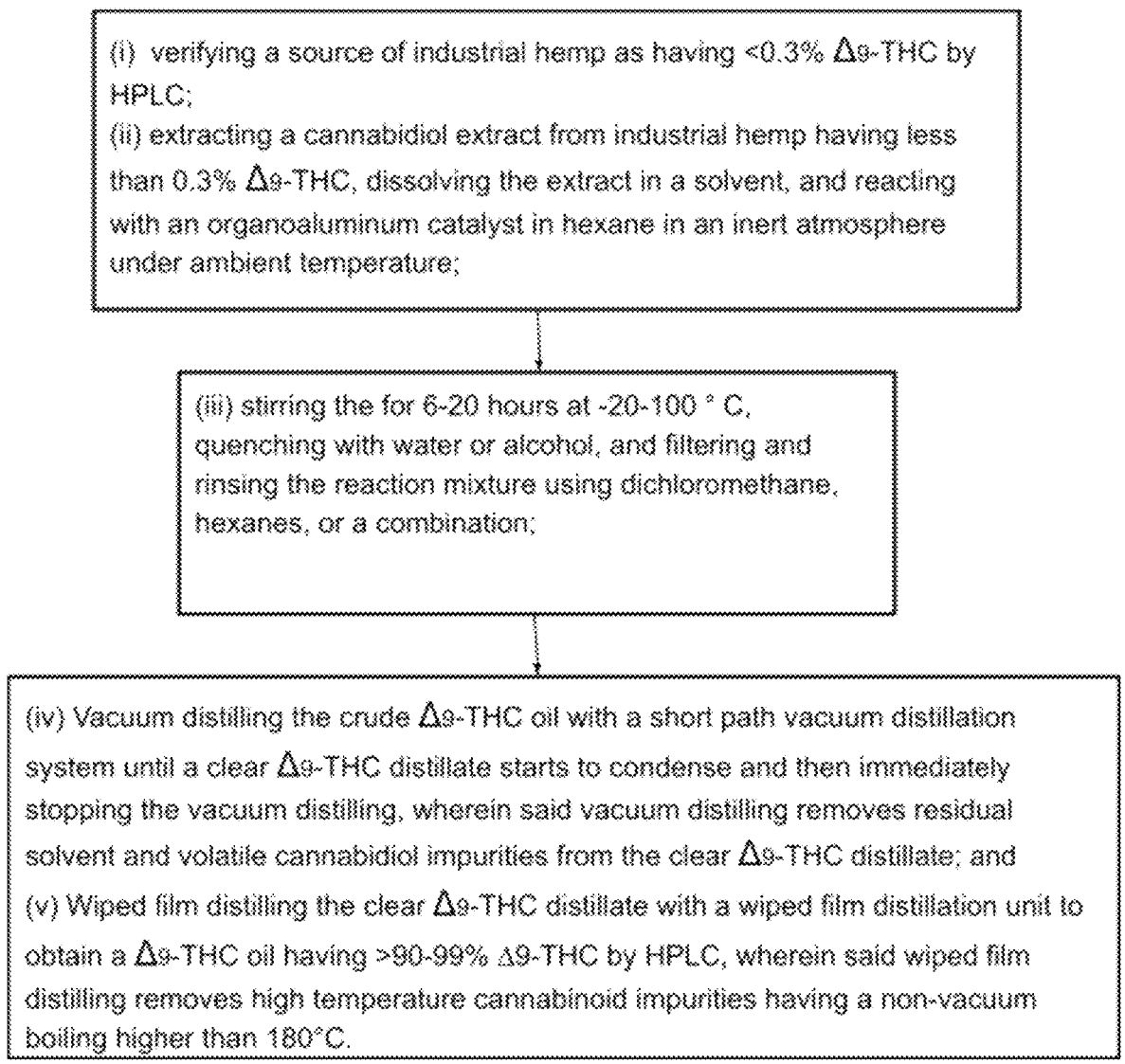
FIG. 5 is a process flowchart showing another preferred embodiment of the inventive process described and claimed herein for (i) verifying a source of industrial hemp as having <0.3% $\Delta^9$-THC by HPLC; (ii) extracting a cannabidiol extract from industrial hemp having less than 0.3% $\Delta^9$-THC, dissolving the extract in a solvent, and reacting with an organoaluminum catalyst in hexane in an inert atmosphere under ambient temperature, (iii) stirring the for 6-20 hours at −20° C. to 70° C., quenching with water or alcohol, and filtering and rinsing the reaction mixture using dichloromethane, hexanes, or a combination; (iv) Vacuum distilling at 15-20 mTorr the crude $\Delta^9$-THC oil with a short path vacuum distillation system until a clear $\Delta^9$-THC distillate starts to condense and then immediately stopping the vacuum distilling, wherein said vacuum distilling removes residual solvent and volatile cannabidiol impurities from the clear $\Delta^9$-THC distillate; and (v) Wiped film distilling the clear $\Delta^9$-THC distillate with a wiped film distillation unit to obtain a $\Delta^9$-THC oil having >90-99% $\Delta^9$-THC by HPLC, wherein said wiped film distilling removes high temperature cannabinoid impurities having a non-vacuum boiling higher than 180° C.

Provided herein are methods for obtaining CBD from industrial hemp plant having 0.3% or less $\Delta^9$-THC (also known as federally compliant hemp) and converting the CBD to a highly pure $\Delta^9$-THC. The reaction mixture can be manipulated by time, temperature, and catalyst concentration to produce oils at different purities depending on the goal of the reaction. The method of converting CBD yields an essentially pure $\Delta^9$-THC with potency greater than 90%. This process is completed by introducing cannabidiol and adding it to an organic solvent with a catalyst to form a reaction mixture, loading the mixture into a reaction vessel, heating the solution to the preferred temperature, allowing it to reflux for the preferred duration, quenching the reaction mixture when complete, removing the aqueous phase, recovering the solvent, stripping the terpenes and distilling the crude residue to form an essentially pure $\Delta^9$-THC oil.

Essentially pure is defined as greater than 90% presence of $\Delta^9$-THC on a weight to weight basis as detected by HPLC. Such purity of $\Delta^9$-THC is generally accepted as a pharmaceutical, nutraceutical, skin care and/or cosmetic compositions. Additionally, the method consists of the ability not only to produce high purity $\Delta^9$-THC (i.e. 90% to 99.9%) but also to scale up from converting hundreds of grams of CBD to the ability to convert hundreds of kilograms of CBD while maintaining said high purity $\Delta^9$-THC (i.e. 90% to 99.9%). In essence the purity of said $\Delta^9$-THC is considered essentially pure (i.e. 90% to 99.9%) on a weight to weight percent basis of the total composition.

More specifically, in one embodiment the invention relates to a process having the steps comprising: obtaining CBD distillate or isolate from industrial hemp plant that is less than 0.3% $\Delta^9$-THC, dissolving CBD distillate or CBD isolate in dichloromethane (DCM) to create a homogenized mixture; adding the homogenized mixture to a reactor vessel continuously purged with an inert gas and adding a 10 mol % solution of organoaluminum catalyst in hexane slowly over 30 minutes at a temperature of 18-26° C. to create a reaction mixture; stirring the reaction mixture for approximately 6-20 hours at a temperature of −20° C. to about 70° C.; quenching the reaction mixture with water or a $C_2$-$C_4$ alcohol, and stirring for 1 hour; filtering the reaction mixture through a filter of diatomaceous earth, perlite, or cellulose to collect a filtrate, and rinsing the filter and reaction vessel with a rinse solvent selected from dichloromethane, hexanes, or a combination of both, and combining the filtrate and the rinse solvent to obtain a combined filtrate and rinse; and performing a split path distillation of the combined filtrate and rinse, wherein the split path distillation comprises a short path distillation and a wiped film distillation to remove terpenes, high volatiles, or high boiling point cannabinoids from the combined filtrate and rinse, to obtain a $\Delta^9$-THC oil comprising over 90% $\Delta^9$-THC and trace amounts of CBD.

In another preferred embodiment, the process comprises wherein the CBD isolate is extracted from natural hemp containing 0.3% of less $\Delta^9$-THC, wherein the solvent is dichloromethane; wherein the inert gas is Argon gas or Nitrogen gas; wherein the organoaluminum catalyst is tri-isobutylaluminum ($iBu_3Al$); wherein quenching uses water; wherein the filter is a diatomaceous earth filter; wherein split path distillation comprises short path distillation first to obtain a main portion separated from a heads portion and a tails portion, followed by wiped film distillation of the main portion; and, wherein the $\Delta^9$-THC oil comprises 95% or greater $\Delta^9$-THC and 3% or less unreacted CBD.

In another preferred embodiment, the process comprises wherein the CBD isolate is extracted from natural hemp containing 0.3% of less $\Delta^9$-THC, wherein the solvent is dichloromethane; wherein the inert gas is Argon gas or Nitrogen gas; wherein the organoaluminum catalyst is tri-isobutylaluminum ($iBu_3Al$); wherein quenching uses water followed by sodium hydroxide followed by additional water; wherein the filter is a diatomaceous earth filter; wherein split path distillation comprises short path distillation first to obtain a main portion separated from a heads portion and a tails portion, followed by wiped film distillation of the main portion; and, wherein the $\Delta^9$-THC oil comprises 95% or greater $\Delta^9$-THC and 3% or less unreacted CBD.

In another preferred embodiment, the process comprises wherein the CBD isolate is extracted from natural hemp containing 0.3% of less $\Delta^9$-THC, wherein the solvent is dichloromethane; wherein the inert gas is Argon gas or Nitrogen gas; wherein the organoaluminum catalyst is tri-isobutylaluminum ($iBu_3Al$); wherein quenching uses water followed by base such as sodium hydroxide or potassium hydroxide followed by aqueous ammonia followed by additional water to afford a granular filterable precipitate; wherein the filter is a diatomaceous earth filter; wherein split path distillation comprises short path distillation first to obtain a main portion separated from a heads portion and a tails portion, followed by wiped film distillation of the main portion; and, wherein the $\Delta^9$-THC oil comprises 95% or greater $\Delta^9$-THC and 3% or less unreacted CBD.

In a preferred embodiment, the invention relates to a process for the preparation of a high purity $\Delta^9$-tetrahydrocannabinol ($\Delta^9$-THC) product compound of the formula shown in FORMULA 1 describing the chemical structure of $\Delta^9$-THC.

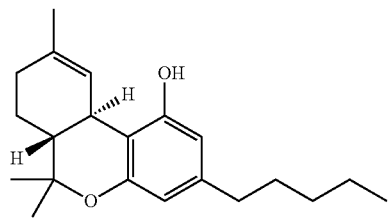 [SMILES: CCCCCc1cc(O)c2c(c1)OC(C)(C)[C@@H]1CCC(C)=C[C@@H]21]

The final high purity $\Delta^9$-tetrahydrocannabinol ($\Delta^9$-THC) is preferably derived from Cannabidiol isolate (CBD isolate) described in FORMULA 2.

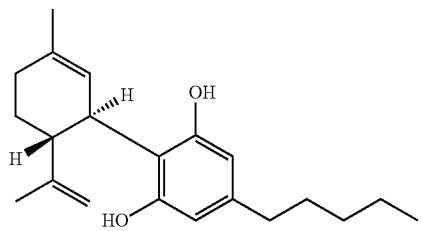 [SMILES: C=C(C)[C@@H]1CCC(C)=C[C@H]1c1c(O)cc(CCCCC)cc1O]

It can also be derived from CBD Distillate or a combination thereof. As the scale of these reactions increases, the control over the process becomes more difficult, due to the exothermic reaction that results from such mixtures. The combination of a CBD isolate solution in a solvent such as dichloromethane (DCM) with the slow addition of an organoaluminum catalyst, results in much higher levels of $\Delta^9$-THC than other metal catalyst or acid previously tested such as aluminum chloride or boron trifluoride diethyl etherate. Running the reaction in a solvent such as dichloromethane (DCM) at reflux temperatures below its boiling point, further increases the conversion of CBD to $\Delta^9$-THC. Hence, the method of the present invention, by the slow addition of an organoaluminum catalyst, such as triisobutylaluminum ($iBu_3Al$) in hydrocarbon solution, in a CBD isolate that is dissolved in DCM at a temperature below its boiling point, gives vastly improved selectivities for the production of $\Delta^9$-THC over its unwanted isomers found in the prior art. The temperature of the reaction may occur at room temperature or a temperature below the boiling point of DCM to maximize the rate of conversion of $\Delta^9$-THC.

Further, the cyclization of cannabidiol to $\Delta^9$-THC is a notoriously difficult reaction to control and carry out selectively. Previously, catalysts, such as $BF_3OEt_2$, (boron trifluoride diethyl etherate) or aluminum chloride have been used. These can induce isomerization of the desired $\Delta^9$-THC isomer to the thermodynamically more stable $\Delta^8$-THC isomer, which is very difficult to separate from the product. Moreover, cyclization of the phenol unit can occur onto the endocyclic double bond to give significant levels of iso-THC derivatives, which are also very difficult to remove. The method of the present invention, by using organoaluminum-based Lewis acid catalysts, gives vastly superior selectivities in this cyclization. For example, with boron trifluoride diethyl etherate, yields of $\Delta^9$-THC are approximately 50-60% at best, with ca. 20% iso-THC and the inherent problem of isomerization of the $\Delta^9$-THC to the $\Delta^8$-THC isomer by the strong Lewis acid. Extended reaction time favors the double bond isomerization to $\Delta^8$-THC. In contrast, when the method of the present invention is used as described herein, e.g., when triisobutylaluminum in hydrocarbon solution is used, yields of $\Delta^9$-THC are >90% with <2% iso-THC with practically no isomerization of the desired product to $\Delta^8$-THC.

Any of the processes herein may include wherein quenching uses water followed by base such as sodium hydroxide or potassium hydroxide followed by aqueous ammonia followed by additional water to afford a granular filterable precipitate.

Any of the processes herein may include a final basic adjustment step to remove alumina in the final product.

The invention described below is a process to produce an essentially pure $\Delta^9$-tetrahydrocannabinol ($\Delta^9$-THC) oil. The original CBD used for the reaction is obtained from an industrial hemp-based extract containing less than 0.3% $\Delta^9$-THC.

Cannabidiol is further dissolved in an organic solvent, such as dichloromethane, and cyclized by an organometallic compound. The resulting crude residue is further purified by short path, fractional, or vacuum distillation to produce an essentially pure $\Delta^9$-tetrahydrocannabinol oil.

The procedure for converting cannabidiol (CBD) to $\Delta^9$-tetrahydrocannabinol consists of a cannabidiol added to an organic solvent with a catalyst to form a reaction mixture. The solution is loaded into a reaction vessel for processing. The reaction mixture is either cooled, held at room temperature or heated to preferred temperature below the boiling point of the solvent. The reaction mixture is mixed for preferred duration depending on the thermodynamic conditions to yield the highest levels of $\Delta^9$-THC. The reaction mixture is quenched with a neutralizing solution. The mixture is separated into an aqueous phase and organic phase. The aqueous layer is drained. The organic solvent is evaporated to leave a crude $\Delta^9$-tetrahydrocannabinol residue. The crude $\Delta^9$-THC is loaded into a boiling flask. The Rashig rings are added to the distillation head. The solution is heated up to a specific temperature. Any remaining terpenes, plant material, or solvent is condensed. Crude $\Delta^9$-THC either continues on to be distilled in short path or is loaded into wiped film for distillation. The crude residue is distilled to concentrate the $\Delta^9$-tetrahydrocannabinol ($\Delta^9$-THC) at scale. At the end of the procedure, essentially pure $\Delta^9$-tetrahydrocannabinol ($\Delta^9$-THC) oil is collected. The final composition of the product is essentially pure $\Delta^9$-THC at a purity of greater than 90% and preferably even greater than 95% on a weight to weight percent basis as measured by HPLC. The remaining composition consists of the original CBD isolate at a concentration of a few percent up to 3% on a weight to weight percent basis as measured by HPLC.

The preferred embodiment uses dichloromethane (DCM) as the organic solvent. Other solvents do not work to provide the high percentage of purity desired, >90% $\Delta^9$-THC.

Although, it is contemplated within the scope of the invention to use this organoaluminum catalyst to obtain lower percentages of $\Delta^9$-THC, e.g. 20-50% in a final $\Delta^9$-THC oil. Any of these embodiments herein may include where the organic solvent comprises ethanol, methanol, isopropanol, ethyl acetate, acetone, acetonitrile, dimethylfuran, dimethyl sulfoxide, toluene, butane, hexane, pentane, heptane, methylene chloride (dichloromethane), ethylene dichloride, (dichloroethane), tetrahydrofuran, benzene, chloroform, purified water, diethyl ether, xylene, and combinations or mixtures thereof.

Any of the preferred embodiments herein may include where the catalyst may be an organoaluminum based catalyst compound comprising of triisobutylaluminum (iBu$_3$Al) in hydrocarbon solution, triisobutylaluminum, or triethylaluminum, and diethylaluminum sesquachloride in a hydrocarbon solvent.

Any of the preferred embodiments herein may include where the organoaluminum catalyst is selected from the group consisting of a trialkyl- or triarylaluminum, dialkyl- or diarylaluminum halide, alkylarylaluminum halide, dialkyl- or alkylaryl- or diarylaluminum alkoxide or aryloxide, dialkyl- or alkylaryl- or diarylaluminum thioalkoxide or thioarylate, dialkyl- or alkylaryl- or diarylaluminum carboxylate, alkyl- or arylaluminum dihalide, alkyl- or arylaluminum dialkoxide or diaryloxide or alkylaryloxide, alkyl- or arylaluminum dithioalkoxide or dithioarylate, alkyl- or arylaluminum dicarboxylate, aluminum trialkoxide or triaryloxide or mixed alkylaryloxide, aluminum triacylcarboxylate, and mixtures thereof.

Any of the preferred embodiments herein may include where the organoaluminum catalyst is a C1-C30 alkylaluminum-based catalyst, or more specifically the organoaluminum-based Lewis acid catalyst is ethyl aluminum dichloride, diethylaluminum chloride, diethylaluminum sesquichloride, isobutylaluminum dichloride, diisobutylaluminum chloride, or mixtures thereof.

Any of the preferred embodiments herein may include where the trialkylaluminum is trimethylaluminum, triethylaluminum, triisopropylaluminum, triisobutylaluminum, trioctylaluminum, or tridecylaluminum.

Any of the preferred embodiments herein may include where the trialkylaluminum is triisobutylaluminum.

Any of the preferred embodiments herein may include where the organoaluminum catalyst is in an amount of from about 0.5 mol % to about 100 mol % with respect to the amount of CBD charged, the amount put in the reactor.

Any of the preferred embodiments herein may include where said organoaluminum catalyst in an amount of from about 5 mol % to about 15 mol % with respect to the amount of CBD charged.

Any of the preferred embodiments herein may include where the catalyst may be hydrolyzed with isopropyl alcohol, or another alcohol. The reaction can further be quenched with water.

Any of the preferred embodiments may include where quenching uses water followed by aqueous base such as sodium hydroxide or potassium hydroxide, optionally followed by aqueous ammonia, and then followed by additional water to afford a granular filterable precipitate.

Any of the preferred embodiments herein may include where the reaction mixture containing an organic and non-organic mixture is then separated and the organic fraction is further treated to remove the solvent from the desired $\Delta^9$-THC fraction. In some embodiments a separation funnel can be used to separate the organic phase. The organic fraction is filtered through celite before being loaded into the evaporation.

Any of the preferred embodiments herein may include where the reaction IS carried out under an inert atmosphere with an inert gas. In some embodiments the inert gas is nitrogen or argon, and/or equivalent gas, or a mixture of argon and nitrogen.

Any of the preferred embodiments herein may include where the process includes an additional aprotic solvent selected from toluene, hexane, heptane, xylene, chloroform, 1,2-dichloroethane, dichloromethane, or a mixture thereof, and preferably the solvent is dichloromethane.

Any of the preferred embodiments herein may include where said stirring is carried out at a temperature of from about −20° C. to about 70° C., or more particularly said stirring is carried out at a temperature of from about −10° C. to about 70° C., or said stirring is carried out at a temperature of from about 0° C. to about 40° C., or said stirring is carried out at a temperature of from about 10° C. to about 35° C.

Any of the preferred embodiments herein may include where the process may comprise an additional purification method selected from the group consisting of chromatography, and countercurrent extraction.

Any of the preferred embodiments herein may include where the starting CBD distillate or CBD isolate is selected from the group consisting of a crude CBD extract, a CBD Isolate, a CBD distillate, and combinations thereof.

Any of the preferred embodiments herein may include wherein Kief is added to the CBD distillate or isolate. In a preferred embodiment, the Kief is 1-2% by weight. In other preferred embodiments, the Kief may include 0.1-1.0% by weight.

Any of the preferred embodiments herein may include where the invention is the $\Delta^9$-THC oil made according to the processes described and claimed herein.

Any of the preferred embodiments herein may include where the invention comprises the $\Delta^9$-THC oil made by the processes herein and a pharmaceutically acceptable carrier.

Any of the preferred embodiments herein may include where the invention comprises the $\Delta^9$-THC oil formulated as a pharmaceutical composition as a tincture, a gummi, or fast melt tab comprising: (i) >90% pure $\Delta^9$-THC oil at a dosage of 1-500 mg/dose, and (ii) a pharmaceutically acceptable carrier comprising a dietary wax, an optional secondary dietary oil, an optional secondary solvent and/or surfactant at 0.1-10% w/v, and an optional antioxidant, and an optional sweetener or flavorant.

Any of the preferred embodiments herein may include where the invention comprises the $\Delta^9$-THC oil formulated as a pharmaceutical composition as a tincture, a gummi, or fast melt tab comprising: (i) >90% pure $\Delta^9$-THC oil at a dosage of 1-500 mg/dose, and (ii) a pharmaceutically acceptable carrier comprising: dietary wax selected from the group consisting of bees wax, plant waxes, very long chain fatty acid waxes, and mixtures thereof, a dietary oil selected from the group consisting of medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglycerides, MCT or LCT, sesame oil, vitamin E, soybean oil, vegetable oil, corn oil, olive oil, peanut oil, coconut oil, palmseed oil, and mixtures thereof, and an optional secondary solvents selected from the group consisting of a very long chain fatty alcohol (C24-C34), ethanol, glycerol, propylene glycol, and polyethylene glycols.

Any of the preferred embodiments herein may include where the invention comprises a topical composition comprising the $\Delta^9$-THC oil in a topical formulation for skin care and cosmetic use.

Any of the preferred embodiments herein may include where the invention comprises a topical composition comprising the $\Delta^9$-THC oil formulated as a topical formulation for skin care and cosmetic use, at a dosage of 1-500 mg/dose, said topical composition comprising: (i) >90% pure $\Delta^9$-THC oil, and (ii) a carrier formulation comprising: a self-emulsifying wax, a polyol, a fatty alcohol, a moisturizer, a hydrocarbon moisturizer/occlusive, an emulsifier, an antioxidant, and optionally a fragrance, a stabilizer, a skin conditioner, Aloe Barbadensis Leaf Juice, a surfactant, an anti-inflammatory, and a preservative.

Any of the preferred embodiments herein may include where the invention comprises a topical composition comprising the $\Delta^9$-THC oil formulated as a topical formulation for skin care and cosmetic use, at a dosage of 1-500 mg/dose, said topical composition comprising: (i) >90% pure $\Delta^9$-THC oil, and (ii) a carrier formulation comprising: a self-emulsifying wax comprising glyceryl stearate, and/or PEG-100 stearate, a polyol comprising glycerin, a fatty alcohol comprising cetyl alcohol, a moisturizer comprising allantoin, a hydrocarbon moisturizer/occlusive comprising petrolatum, an emulsifier comprising steareth-21, an antioxidant comprising tocopheryl acetate, and optionally a fragrance, a stabilizer comprising xanthan gum, a skin conditioner comprising dipotassium glycyrrhizate, Aloe Barbadensis Leaf Juice, a surfactant comprising triethanolamine, an anti-inflammatory comprising bisabolol), and a preservative comprising disodium EDTA.

Any of the preferred embodiments herein may include where the invention comprises a topical composition comprising the $\Delta^9$-THC oil formulated as a cream, an ointment, foam, gel, lotion, ointment, paste, spray, or solution, comprising: (i) >90% pure $\Delta^9$-THC, and a topical carrier selected from the group consisting of cream, ointment, foam, gel, lotion, ointment, paste, spray, and solution, wherein the cream, ointment, gel, lotion, ointment, paste is a water-in-oil or oil-in-water emulsion containing less than 20% water, greater than 50% hydrocarbons, waxes and/or polyols, and includes a surfactant to create a semi-solid, spreadable composition, wherein the foam is a cream or ointment packaged in a pressurized container and delivered with a gas, wherein the spray is a liquid packaged in a pressurized container and delivered with a gas, wherein the solution is a liquid packaged in a container and delivered with an alcohol.

Any of the preferred embodiments herein may include where the invention comprises a nutraceutical composition comprising the $\Delta^9$-THC oil in a nutraceutical formulation.

Any of the preferred embodiments herein may include where the invention comprises a method of administering the $\Delta^9$-THC oil to a patient in need thereof, comprising formulating the $\Delta^9$-THC oil as an oral or topical composition, wherein the patient has nausea, anxiety, stress, chronic pain, acute pain, or requires an appetite stimulant.

Any of the preferred embodiments herein may include using a signature tracking marker that is added to a product or packaging containing the high purity $\Delta^9$-THC oil made herein.

Any of the preferred embodiments herein may include a process for authenticating the $\Delta^9$-THC oil made according to the high purity process herein, by adding a signature marker to a product or packaging containing the $\Delta^9$-THC oil made according to the high purity process herein, testing the product or packaging for the presence of the signature marker, comparing a test result against a positive control and a negative control, and identifying the product or packaging as authentic if the test result matches the positive control more than the negative control.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Specific Definitions

The terms $\Delta^8$-tetrahydrocannabinol or $\Delta^8$-THC or delta-8-tetrahydrocannbinol refers to 6,6,9-trimethyl-3-pentyl-6a,7,10,10a-tetrahydrobenzo[c]chromen-1-ol (IUPAC 2019-06). $\Delta^8$-THC can be represented by 2D structure as follows:

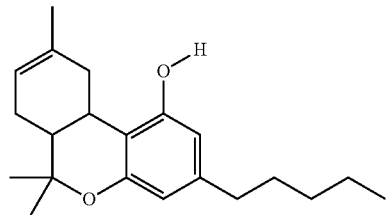 [SMILES: CCCCCc1cc(O)c2c(c1)OC(C)(C)C1CC=C(C)CC21]

The term $\Delta^9$-THC or $\Delta^9$-tetrahydrocannabinol or delta-9-tetrahydrocannbinol refers to (6aR,10aR)-6,6,9-trimethyl-3-pentyl-6a,7,8,10a-tetrahydrobenzo[c]chromen-1-ol (IUPAC 2019-June). $\Delta^9$-THC can be represented by 2D structure as follows:

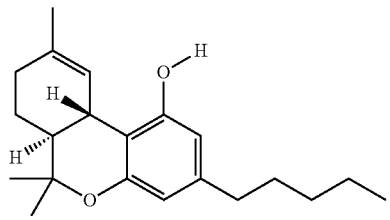

The term "pure" or "essentially pure" or "highly pure" refers to greater than 90% of $\Delta^9$-THC in the final product, and/or from 90-99% of $\Delta^9$-THC in a given final product. Purity may be obtained using HPLC.

FIG. 1 illustrates, using an HPLC chromatograph, the peaks of various cannabinoids. The first to come off at around 90 seconds is cannabidivarinic acid, followed by cannabidivarin at around 1'45". The next peaks, 3-4-5-6-7, fall between 2 minutes and 3 minutes (2'-3') are cannabidiolic acid, cannabigerolic acid, cannabigerol, cannabidiol, and tetrahydrocannabivarin, respectively. Between 4' and 5', the peaks for 8 and 9 are shown for tetrahydrocannabivarinic acid, and cannabidiol (CBD). Between 6' and 7', the peaks for 10 and 11 are $\Delta^9$-tetrahydrocannabinol ($\Delta^9$-THC), and $\Delta^8$-tetrahydrocannabinol ($\Delta^8$-THC). At around the 9 minute (9') mark the number 12 and 13 species are cannabichromene and Δ⁹-tetrahydrocannabinolic acid A. And finally at about 11'30", the cannabichromenic acid comes off.

The term "CBD" refers to cannabidiol and has a molecular weight of 314.47 g/mol.

The term "CBD Distillate" refers to the process of applying high heat (boiling point) to raw extracted oil in a distillation chamber to separate the oil components and obtain highly pure CBD. CBD distillate does not contain or contains only a very small percentage of terpenes.

The term "CBD Isolate" refers to 99% pure CBD created by cooling and crystallizing CBD extract to form a white powder.

The term "hemp" does not include marijuana, and "natural hemp", "industrial hemp", or "hemp" as used herein refers to a variety of Cannabis sativa that contains less than 0.3% Δ⁹-tetrahydrocannabinol (Δ⁹-THC).

The term "cannabinoid" or "cannabinoids" as used herein encompasses at least the following substances: Δ⁸-tetrahydrocannabinol, Δ⁹-tetrahydrocannabinol (THC), cannabinol (CBN), cannabidiol (CBD), cannabigerol (CBG), Δ⁹(11)-tetrahydrocannabinol (exo-THC), cannabichromene (CBC), tetrahydrocannabinol-C3 (THC-C3), tetrahydrocannabinol $^A$ (THC-C4).

Examples of cannabinoids include:

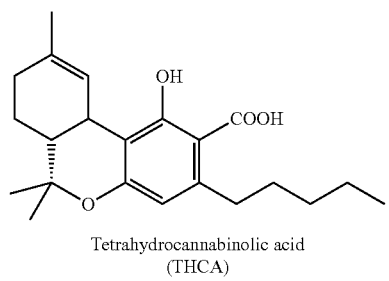

Tetrahydrocannabinolic acid
(THCA)

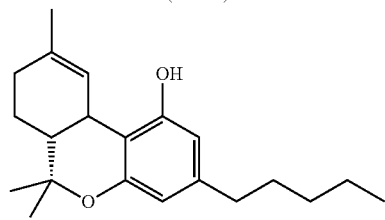

Tetrahydrocannabinol
(THC)

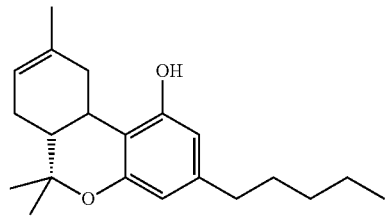

Delta-8-tetrahydrocannabinol
(Delta-8-THC)

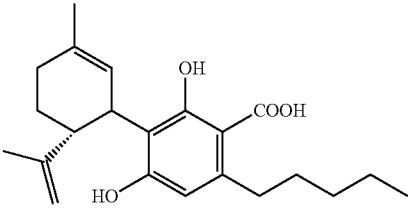

Cannabidiolic acid
(CBDA)

-continued

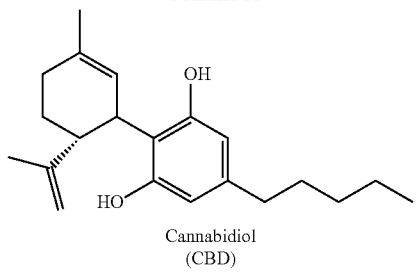

Cannabidiol
(CBD)

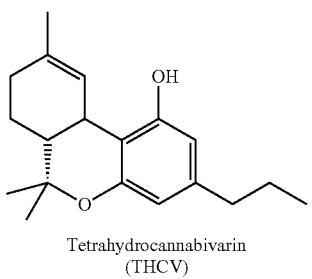

Tetrahydrocannabivarin
(THCV)

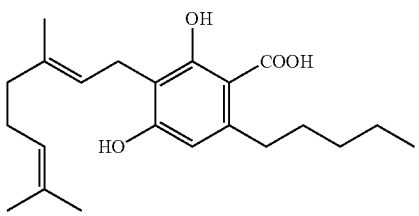

Cannabigerolic acid
(CBGA)

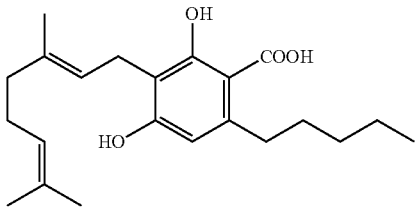

Cannabigerol
(CBG)

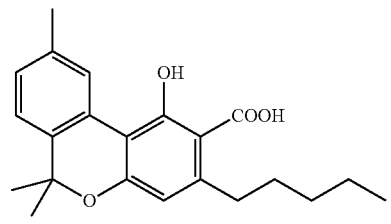

Cannabinolic acid
(CBNA)

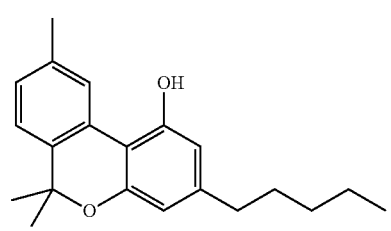

Cannabinol
(CBN)

-continued

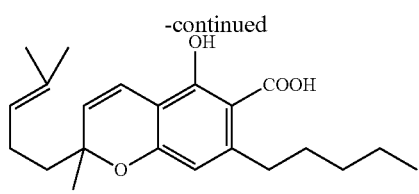

Cannabichromeric acid (CBCA)

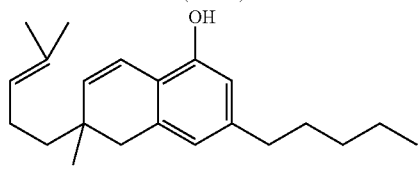

Cannabichromene (CBC)

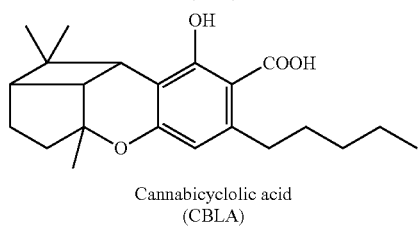

Cannabicyclolic acid (CBLA)

-continued

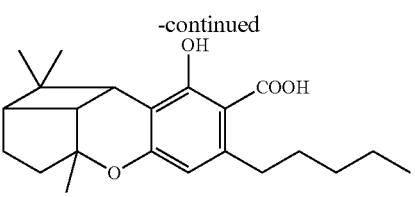

Cannabicyclol (CBL)

*Note: the CBC structure above is intended to contain an oxygen in the ring next to the benzyl.

$\Delta^9$-THC has a published boiling point at about 157° C. at 15-20 mTorr vacuum. $\Delta^8$-THC has a published boiling point at about 177° C. at 15-20 mTorr vacuum. Solvents, non-compliant cannabinoids, and volatile cannabinoids are defined as having a boiling point less than about 160° C. at 15-20 mTorr vacuum. In distillation, as used herein, these low temperature compounds are known as "heads". High boiling point cannabinoids (vacuum) are defined herein as cannabinoids having a boiling point above about 180° C. at 15-20 mTorr vacuum, and do not include, by definition $\Delta^8$-THC. In distillation, as used herein, these high temperature compounds are known as "tails", with the "main" being $\Delta^8$-THC, its crude oils, its distillates, and its purified oils.

Boiling points differ among cannabinoids. This permits separation by distillation techniques.

TABLE - Relevant cannabinoid structures and boiling points

| STRUCTURE | NAME | B.P. |
|---|---|---|
| 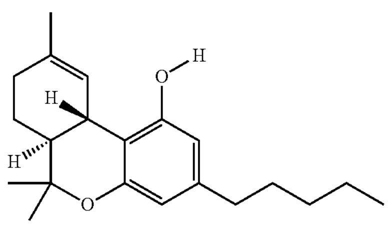 | $\Delta^9$ - THC<br>$\Delta^9$ - tetrahydrocannabinol | 157° C. at<br>15-20 mTorr<br>vacuum |
| 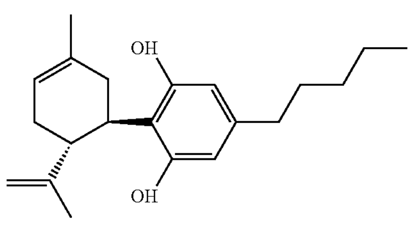 [SMILES: C=C(C)[C@@H]1CC=C(C)C[C@H]1c1c(O)cc(CCCCC)cc1O] | CBD cannabidiol | 160-180° C.<br>15-20 mTorr<br>vacuum |
| 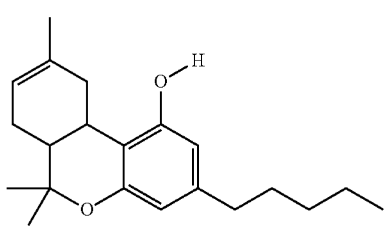 [SMILES: CCCCCc1cc(O)c2c(c1)OC(C)(C)C1CC=C(C)CC21] | $\Delta^8$ - THC<br>$\Delta^8$ - tetrahydrocannabinol | 175-178° C.<br>15-20 mTorr<br>vacuum |

TABLE

Cannabinoid b.p. - lowest to highest, under 15-20 mTorr vacuum

| NAME | B.P. ° C. |
|---|---|
| THCA | 105 |
| CBG | 105 |
| B-CARYOPHYLLENE | 119 |
| p-CYMENE | 134 |
| a-PINENE | 156 |
| $\Delta^9$-THC | 157 |
| CBD | 160-180 |
| B-MYRCENE | 166-168 |
| $\Delta^8$-THC | 175-178 |
| 1,8-CINEOLE | 176 |
| d-LIMONENE | 177 |
| CBC | 185 |
| CBN | 185 |
| LINALOOL | 198 |
| TERPINEOL-4-OL | 209 |
| a-TERPINEOL | 218 |
| THCV | 220 |
| PULEGONE | 224 |
| APIGENIN | 270 |
| QUERCETIN | 302 |
| CBDA | 316-531 |
| B-SITOSTEROL | 414 |

The term "extraction" refers to a process for obtaining raw Cannabinoid extract from dried Hemp plant material. Non-limiting illustrative processes include $CO_2$ extraction, liquid chromatography, solvent extraction, and olive oil extraction. Extracts contain other plant components—major and minor cannabinoids, terpenes, and flavonoids—that isolates do not.

The term "$CO_2$ extraction" refers to a process for obtaining CBD from industrial hemp that comprises by way of illustration in a non-limiting example the following steps: —extraction with supercritical $CO_2$ (e.g. 60° C., 250 bar); —decarboxylation (e.g. 80° C., 2 hours); and —separation in a high pressure column (using $CO_2$ as solvent). The method is shown to yield an extract containing CBD in approximately 90% purity.

The term "Winterization" refers to combining extracted CBD oil with ethanol and freezing overnight, which is then filtered to remove fats and other impurities, and the filtrate is heated to evaporate the ethanol.

The term "Kief" refers to a high potency THC composition consisting of accumulated trichomes, or resin glands, sifted from cannabis flowers through a mesh screen or sieve. Trichomes are the crystal-like hairs that cover the cannabis flower bud. Trichomes secrete a sticky resin containing the terpenes and cannabinoids that give cannabis its unique qualities. As concentrated resin glands, kief occurs as a fine powder and is a potent form of cannabis. More simply, Kief is a cannabis concentrate that contains from about 50%-80% THC and includes both cannabinoids and terpenes.

The term "optically active" or "chiral" CBD refers to the CBD extract comprising an optically active chiral CBD having an R,R or trans(−) rotation. CBD is known to have two chiral centers. Natural, plant-based CBD has this R,R or trans(−) rotation, specifically −125 deg. to about −129 deg. in alcohol. Contrast this with synthetic (crystalline) CBD that is not optically pure. This is due to the fact that synthetic CBD is formed from limonene, with the freebase treated with ethanol. The consequence of using limonene, which is sourced from California or Florida, is that the resulting synthetic CBD is not optically pure, and when synthetic CBD is used to form $\Delta^9$-tetrahydrocannabinol, the reaction cannot provide optically pure $\Delta^9$-tetrahydrocannabinol isomer, without additional processing to form a crystalline ester of the $\Delta^9$-tetrahydrocannabinol to obtain a single diastereomer, and then hydrolyzing back from the ester to obtain an optically pure $\Delta^9$-tetrahydrocannabinol. Thus using synthetic CBD sourced from California or Florida limonene can result in a "California isomer" or "Florida isomer" of an optically impure $\Delta^9$-tetrahydrocannabinol isomer.

The term "organic solvent" refers, in a preferred embodiment, to dichloromethane (DCM). In alternative embodiments, the organic solvent may refer to ethanol, methanol, isopropanol, acetone, toluene, hexane, pentane, heptane, methylene chloride (dichloromethane), ethylene dichloride (dichloroethane), tetrahydrofuran, benzene, chloroform, purified water, diethyl ether, and/or xylene.

The term "catalyst" refers to an organoaluminum catalyst is selected from the group consisting of a trialkyl- or triarylaluminum, dialkyl- or diarylaluminum halide, alkylarylaluminum halide, dialkyl- or alkylaryl- or diarylaluminum alkoxide or aryloxide, dialkyl- or alkylaryl- or diarylaluminum thioalkoxide or thioarylate, dialkyl- or alkylaryl- or diarylaluminum carboxylate, alkyl- or arylaluminum dihalide, alkyl- or arylaluminum dialkoxide or diaryloxide or alkylaryloxide, alkyl- or arylaluminum dithioalkoxide or dithioarylate, alkyl- or arylaluminum dicarboxylate, aluminum trialkoxide or triaryloxide or mixed alkylaryloxide, aluminum triacylcarboxylate, and mixtures thereof. In a preferred embodiment, the organoaluminum catalyst is a $C_1$-$C_{30}$ alkylaluminum-based catalyst. In a more preferred embodiment, the organoaluminum-based Lewis acid catalyst is ethyl aluminum dichloride, diethylaluminum chloride, diethylaluminum sesquichloride, isobutylaluminum dichloride, diisobutylaluminum chloride, or mixtures thereof. In another preferred embodiment, the trialkylaluminum is trimethylaluminum, triethylaluminum, triisopropylaluminum, triisobutylaluminum, trioctylaluminum, or tridecylaluminum. In another preferred embodiment, the catalyst is 1-2 molar triisobutylaluminum in hexane or 1 molar triisobutylaluminum in toluene. In another preferred embodiment, the catalyst is in an amount of from about 0.5 mol % to about 100 mol % with respect to the homogenized mixture, or in an amount of from about 5 mol % to about 15 mol % with respect to the homogenized mixture.

The term "Short Path Distillation" refers to distillation having a minimal number of plates, e.g. 1 plate or 3 plates, and, refers to slowly heating CBD oil until extraneous substances having a different boiling point than CBD, such as heads (terpenes and high volatiles), and tails (high boiling point cannabinoids), are vaporized into a distillation tube, condensed by cooling coils, and separated, leaving purified CBD oil. Short Path distillation is generally not known for scalability into large batches. Short path distillation produces a high-quality distillate, but is limited in scale.

Short path distillation utilizes an apparatus with a multi-position receiver and condensing head. This process is very limited in scale and production, but can produce high-quality distillate with an experienced operator. Crude oil is heated in a boiling flask with a magnetic stirrer. The condensing head is jacketed and requires a recirculating "chiller" with hot water to cool the condensing head to condense the cannabinoid vapor back into a liquid form, with the different fractions condensing into different receiving flasks.

A short path will typically have 3 fractions—heads (terpenes and high volatiles), main body (THC/CBD), and tails (high boiling point cannabinoids).

The term "Thin Film Distillation" or "Wipe Film Distillation" refers to adding CBD crude oil, under vacuum, to the top of a heated vertical cylinder on a rotating plate. As the oil enters the cylinder (a jacketed, chilled condensing head), it encounters the rotating, specially designed wipers or rollers that create and renew a thin film on the heated surface. A long condenser in the middle of the wipers in the evaporator body, cooled with recirculating fluid, condenses the vapor. Receiving vessels collect the distillate and the high temperature residue at the bottom. A recirculating heater maintains the temperature of the feed container and outer jacketed wiped film evaporator body. Refrigerated circulators cool the condenser and cold trap.

Optimizing the feed rate, vacuum, and temperatures is essential to yield the desired component composition in the distillate. This method reduces the exposure time of the oil. With a wiped film extraction, two passes through the system are required to achieve a distillate. As in distillation, wiped film strips the crude of low boiling point compounds first, for example, terpenes and leftover volatiles. Then, during the second pass, the residue is run again to achieve the final CBD distillate.

The term "hexanes" refers to mixed isomers of hexane used as a solvent. The boiling point of hexanes is 68-70° C.

The term "verification" or "compliance" refers to quantitative methods for ensuring a level of less than 0.3% $\Delta^9$-THC of the starting material, the reaction intermediates and reaction mixtures, the crude $\Delta^9$-THC oil, the clear $\Delta^9$-THC distillate, and the highly pure >90% $\Delta^9$-THC oil. Quantitative methods may also be used to detect levels of impurity. Such impurities may include without limitation: $\Delta^8$-THC, solvent, catalyst, terpenes, cannabinoids, and cannabinoid processing-related volatiles.

Quantitative compliance verification methods contemplated as within the scope of the invention include, without limitation, any verification method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

The term "HPLC" refers to high performance liquid chromatography.

The term "normal phase chromatography" is a type of HPLC technique. It separates analytes based on the degree of interaction towards the absorbent, which is polar silica. Therefore, the stationary phase of this type of chromatography is hydrophilic. It can also make hydrophilic interactions with the hydrophilic molecules in the sample mixture. Generally, these interactions include hydrogen bonding, dipole-dipole interactions, etc. Therefore, more non-polar analytes stay longer in the stationary phase, increasing the retention time. Furthermore, the mobile phase in the normal phase chromatography is non-polar and non-aqueous. Therefore, non-polar or hydrophobic analytes in the mixture wash out effectively with the mobile phase at the beginning of the process. Meanwhile, the retention time of analytes reduces with the increasing polarity of the mobile phase. In the present invention, it is contemplated in one embodiment that normal phase chromatography may be used for analysis of the reaction products and purified products from the intermediate steps of the process up to, but not including, the final purification step of the process.

The term "reverse-phase chromatography" is a type of recent HPLC. It has an increased reproducibility of the retention time when compared to normal phase chromatography. Basically, this increase of the reproducibility is achieved by making the stationary phase non-polar. To do that, the surface of the silica stationary phase is modified as R-(Me)$_2$SiCl, where R is a straight-chain alkyl group such as $C_{18}H_{37}$ or $C_8H_{17}$. However, due to the non-polar nature of the stationary phase, less polar analytes in the sample mixture tend to have a higher retention time in contrast to the normal phase chromatography. Moreover, one can increase the retention time by adding more water to the mobile phase, which, in turn, increases the hydrophobic interactions between the non-polar analytes and the stationary phase. Also, the mobile phase of the reverse phase chromatography is polar, washing out polar analytes in the sample mixture. This facilitates the separation of the non-polar analytes in the sample mixture. Furthermore, the surface tension of the mobile phase, as well as its pH, have effects on the retention time. In the present invention, it is contemplated in one embodiment that reverse phase chromatography may be used for analysis of the final purified product from the final step of the purification process.

In contrast, normal phase chromatography refers to a separation method which allows the distribution of components of a mixture between two phases, one of which is a polar stationary phase while the mobile phase is non-polar, whereas reverse phase chromatography refers to the separation method, whose mobile phase is more polar than the stationary phase. Normal phase chromatography uses a polar stationary phase, which is mainly pure silica, while reverse phase chromatography uses a non-polar stationary phase, which is a modified silica substrate with long hydrophobic long chains. Normal phase chromatography uses a non-polar, non-aqueous solvent as the mobile phase, which is mainly chloroform while reverse phase chromatography uses a polar mobile phase, which is mainly water, methanol or acetonitrile. Normal phase chromatography separates polar analytes with high retention time in the column, while reverse phase chromatography separates less polar analytes, which have a high retention time in the column. In normal phase chromatography, the mobile phase carries non-polar analytes at the beginning of the separation while in reverse phase chromatography, the mobile phase carries polar analytes. A non-polar mobile phase increases the retention time of normal phase chromatography while a polar mobile phase increases the retention time of reverse phase chromatography. Analytes can be eluted by increasing the polarity of the mobile phase in the normal phase chromatography while the analytes can be eluted by decreasing the polarity of the mobile phase in the reverse phase chromatography. The stationary phase of normal phase chromatography contains a layer of water or protic organic solvent while the stationary phase of reverse phase chromatography does not contain water or a layer of protic solvent.

EXAMPLES

The invention is described below by means of an example, although the invention is not limited to this example.

The present invention relates to a process for the preparation of a high purity $\Delta^9$-tetrahydrocannabinol product compound of the formula:

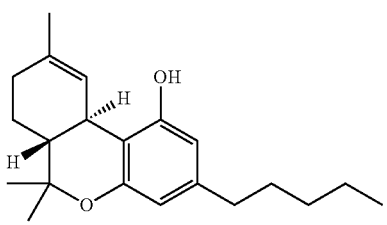

FORMULA 1. Chemical Structure of $\Delta^9$-Tetrahydrocannabinol

The final high purity $\Delta^9$-tetrahydrocannabinol ($\Delta^9$-THC) is preferably derived from Cannabidiol distillate or CBD isolate, or a combination thereof. In a preferred embodiment the starting material is Cannabidiol Isolate.

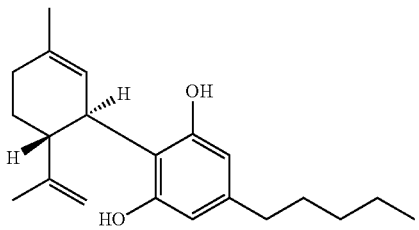

FORMULA 2. Chemical Structure of Cannabidiol (CBD) Extracted from Hemp

As the scale of these reactions increases, the control over the process becomes more difficult, considering the exothermic nature of the reaction. By adding the organoaluminum catalyst slowly, the reactions of the present invention can proceed with practically no overreaction to cyclized products. The combination of a CBD isolate solution in a solvent such as dichloromethane (DCM) with the slow addition of an organoaluminum catalyst, results in much higher levels of $\Delta^9$-THC. Running the reaction in dichloromethane (DCM) at temperatures below its boiling point further increases the conversion of CBD to $\Delta^9$-THC. Hence, the method of the present invention, by the slow addition of an organoaluminum catalyst in a CBD isolate that is dissolved in DCM at a temperature below its boiling point, gives vastly improved selectivities for the production of $\Delta^9$-THC over its unwanted isomers found in the prior art.

Cyclization of cannabidiol to $\Delta^9$-THC, without converting to the thermodynamically more stable $\Delta^8$-isomer, uses organoaluminum-based Lewis acid catalysts to obtain yields of $\Delta^9$-THC are >90% with <2% iso-THC with practically no isomerization of the desired product to $\Delta^8$-THC.

The organoaluminum-based Lewis acid catalyst used in the method of the present invention can be a trialkyl- or triarylaluminum, dialkyl- or diarylaluminum halide, alkylarylaluminum halide, dialkyl- or alkylaryl- or diarylaluminum alkoxide or aryloxide, dialkyl- or alkylaryl or diarylaluminum thioalkoxide or thioarylate, dialkyl- or alkylaryl or diarylaluminum carboxylate, alkyl- or arylaluminum dihalide, alkyl- or arylaluminum dialkoxide or diaryloxide or alkylaryloxide, alkyl- or aryl aluminum dithioalkoxide or dithioarylate, alkyl- or arylaluminum dicarboxylate, aluminum trialkoxide or triaryloxide or mixed alkylaryloxide, aluminum triacylcarboxylate or mixtures thereof. Suitable examples of organoaluminum-based Lewis acid catalysts include, but are not limited to, trimethylaluminum, triethylaluminum, triisopropylaluminum, triisobutylaluminum, tri-octylaluminum, tridecylaluminum, diethylaluminum chloride, diisobutylaluminum chloride, diethylaluminum sesquichloride, ethyl aluminum dichloride, methylaluminum dichloride, isobutylaluminum dichloride, diethylaluminum ethoxide, diethylaluminum isopropoxide, diisobutylaluminum methoxide, diisobutylaluminum phenoxide, diphenylaluminum isoproproxide, tetraisobutylalumoxane, methylalumoxane, methylaluminum bis-(2,6-di-t-butyl-4-methylphenoxide), diisobutylaluminum acetate, diisobutylaluminum benzoate, diisobutylaluminum trifluoroacetate, diisobutylaluminum isopropoxide, diisobutylaluminum 2,6-di-t-butyl-4-methylphenoxide, isobutylaluminum bis-(2,6-di-t-butyl-4-methylphenoxide), isobutylaluminum diacetate, aluminum trimethoxide, aluminum triisopropoxide, aluminum tri-tert-butoxide, and aluminum trifluoroacetate. Several such catalysts are commercially available or can be prepared from commercially available aluminum reagents, using methods known in the literature, such as described by Ooi and Maruoka, Science of Synthesis, Vol. 7, pp. 131-195, Stuttgart, Germany Thieme (2000), which is hereby incorporated by reference in its entirety.

In one embodiment of the present invention, the organoaluminum-based Lewis acid catalyst is a $C_1$-$C_{30}$ alkylaluminum-based or $C_6$-$C_{30}$ arylaluminum-based substance or mixture. In another embodiment of the present invention, the organoaluminum-based Lewis acid catalyst contains one or more oxygenated substituents bonded to the aluminum which modify the physical properties or performance of the catalyst. In another embodiment of the present invention, the organoaluminum-based Lewis acid catalyst may be made in situ before use by reaction of a precursor aluminum reagent with a modifying substituent. Specifically, the organoaluminum-based Lewis acid catalysts can be catalysts which provide high selectivity for $\Delta^9$-THC at lower levels of catalyst usage and at convenient rates for larger scale preparation. More specifically, the organoaluminum-based Lewis acid catalysts can be catalysts that produce $\Delta^9$-THC with very low levels of isomers (e.g., cis-$\Delta^9$-THC, $\Delta^8$-THC, and iso-THC), as these are difficult to remove from the product and render it difficult to achieve current standards of pharmaceutical purity.

In another embodiment of the present invention, the step of treating is carried out with the organoaluminum-based Lewis acid catalyst in an amount from about 0.5 mol % to about 100 mol % with respect to the first intermediate compound. In yet another embodiment of the present invention, the step of treating is carried out with the organoaluminum-based Lewis acid catalyst in an amount from about 5 mol % to about 15 mol % with respect to the amount of CBD charged.

The step of treating can be carried out in an organic solvent. In one embodiment of the present invention, the solvent is aprotic. Examples of organic solvent include, but are not limited to ethanol, methanol, isopropanol, ethyl acetate, acetone, acetonitrile, dimethylfuran, dimethyl sulfoxide, toluene, butane, hexane, pentane, heptane, methylene chloride (dichloromethane), ethylene dichloride, (dichloroethane), tetrahydrofuran, benzene, chloroform, purified water, diethyl ether, and/or xylene and/or a mixture thereof.

The step of treating can be carried out at a temperature of from about −20° C. to the boiling point of the solvent used for the reaction. In another embodiment of the present invention, the step of treating can be carried out at a temperature of from about 0° C. to about 40° C. In yet in another embodiment of the present invention, the step of treating can be carried out at a room temperature or slightly higher than room temperature to speed up the reaction rate but cannot exceed the boiling point of the solvent. In one non-limiting embodiment, the temperature is below the boiling point of hexanes at 68-70° C. In one non-limiting embodiment, the temperature is below the boiling point of dichloromethane at 39-40° C. In one non-limiting embodiment, the temperature is below the boiling point of toluene at 110-111° C.

The starting product compound is a totally natural substance from natural hemp which contains less than 0.3% $\Delta^9$-THC as a starting material. Furthermore, the CBD is extracted from the hemp and converted to CBD distillate or CBD isolate or a combination thereof.

In another embodiment, the process of the present invention further involves carrying out a method selected from chromatography, countercurrent extraction, and distillation on the product under conditions effective to produce a purified product.

Examples

The following examples are provided to illustrate embodiments of the present invention but are by no means intended to limit its scope.

Example. Extraction of CBD from Industrial Hemp Containing 0.3% or Less $\Delta^9$-THC Dried Hemp plant material is processed, or extracted, to obtain a raw Cannabinoid extract. Non-limiting illustrative processes include $CO_2$ extraction, liquid chromatography, solvent extraction, and olive oil extraction. The extract contains other plant components—major and minor cannabinoids, terpenes, and flavonoids—that isolates do not.

In a non-limiting preferred embodiment, industrial hemp containing 0.3% or less $\Delta^9$-THC is processed using "$CO_2$ extraction" to obtain CBD. Specific steps include: —extraction with supercritical $CO_2$ (e.g. 60° C., 250 bar); —decarboxylation (e.g. 80° C., 2 hours); and —separation in a high pressure column (using $CO_2$ as solvent). The method yields an extract containing CBD in approximately 90% purity.

Example. Extraction of CBD from Hemp Containing 0.3% or less $\Delta^9$-THC, and Winterization Industrial hemp containing 0.3% or less $\Delta^9$-THC is processed using "$CO_2$ extraction" to obtain CBD. Specific steps include: —extraction with supercritical $CO_2$ (e.g. 60° C., 250 bar); —decarboxylation (e.g. 80° C., 2 hours); and —separation in a high pressure column (using $CO_2$ as solvent). The method yields an extract containing CBD in approximately 90% purity. The CBD extracted oil is combined with ethanol and is then frozen overnight. After freezing, the combined CBD-EtOH is then filtered to remove fats and other impurities, and the filtrate is heated to evaporate the ethanol.

The following examples show $\Delta^9$-THC from CBD Distillate.

Example 1. Preparation of $\Delta^9$-THC from CBD Distillate Using Basic Ionic Resin Workup CBD Distillate (15 kg @85% CBD content) was dissolved in dichloromethane (75 liters) in a nitrogen inerted, 150 L cylindrical glass reactor with an overhead stirrer, pressure equalizing addition funnel and a water-cooled reflux condenser to create a homogenized mixture. The reactor was inerted with nitrogen and triisobutylaluminum (6 L of 1 M solution in hexane, 10 mol % catalyst) was then slowly added over 30 minutes at a batch temperature of 26° C. The reaction mixture was stirred for 6 hours at a temperature of 26 to 30° C., at which point the reaction was determined to be complete by TLC and HPLC analysis (<2.0% CBD by HPLC). The solution was quenched with 25 liter of water and stirred for 1 hour, then circulated through a water washed Amberlyst A21 resin column for two hours. The reaction mixture was filtered through celite coated sparkler filter. The reactor and celite cake were rinsed with dichloromethane (5 L) and rinse was added to the clarified batch. The layers were separated, and the aqueous layer was washed with fresh dichloromethane (2.5 L) and this rinse was added to the organic layer. The organic layer was concentrated under reduced pressure. The remaining organic residue was wiped film distilled (165° C. at 15 mTorr vacuum) to afford 8.7 kg (58% yield when corrected for the assay of the starting material) of $\Delta^9$-THC as a clear to light yellow viscous oil. The HPLC analysis of this product was comparable to the assay of earlier batches.

Example 2. Preparation of $\Delta^9$-THC from CBD Distillate, with Aqueous Sodium Hydroxide Workup CBD Distillate (5.0 kg @85% CBD content) was dissolved in dichloromethane (15 liters) in a nitrogen inerted, 50 L cylindrical glass reactor with an overhead stirrer, pressure equalizing addition funnel and a water-cooled reflux condenser to create a homogenized mixture. The reactor was inerted with nitrogen and triisobutylaluminum (2.0 L of 1 M solution in hexane, 10 mol % catalyst) was then slowly added over 3.5 hours at a batch temperature between 18 and 30° C. The reaction mixture was stirred for approximately 6 hours at a temperature of 20 to 25° C., at which point the reaction was determined to be complete by TLC and HPLC analysis (<2.0% CBD by HPLC). The batch was diluted with THF (4 L) and stirred for 15 minutes. The solution was quenched with water (75 mL) followed by 15% NaOH solution (75 g) and then water (235 mL). The quenched batch stirred for 1 hour, then magnesium sulfate (500 g) was added, and the stirring was continued for an additional hour. The alumina containing suspension was clarified through a celite coated sparkler filter. The filter cake was washed with fresh THF (1 L) and the wash was added to the batch. The filtrate was concentrated under reduced pressure using a rotary evaporator until the light solvents stopped distilling. The remaining organic residue was wiped film distilled in two temperature stages (first pass: 160° C. at 15 mTorr vacuum then second pass: 170° C. at 15 mTorr vacuum) to afford 3.83 kg (90% yield when corrected for the assay of the starting material) of $\Delta^9$-THC as a clear to light yellow viscous oil. The HPLC analysis of this product was comparable to the assay of earlier batches.

Example 3. Preparation of $\Delta^9$-THC from CBD Distillate, with Aqueous Ammonia Workup CBD Distillate (1.0 kg @85% CBD content) was dissolved in dichloromethane (3 liters) in a nitrogen inerted, 22 L glass reactor with an overhead stirrer, pressure equalizing addition funnel and a water-cooled reflux condenser to create a homogenized mixture. The reactor was inerted with nitrogen and triisobutylaluminum (400 mL of 1 M solution in hexane, 10 mol % catalyst) was then slowly added over 2 hours at a batch temperature between 18 and 30° C. The reaction mixture was stirred for approximately 6 hours at a temperature of 20 to 25° C., at which point the reaction was determined to be complete by TLC and HPLC analysis (<2.0% CBD by HPLC). The reaction was quenched with water (15 mL) and when the active catalyst was quenched, the reaction mixture was rotary evaporated under reduced pressure to ca. 1 L volume. The batch was diluted with methyl tert-butyl ether (MtBE) (2 L) and the mixture was stirred. To the stirred solution was added 28% aqueous ammonia solution (25 mL) followed by additional water (50 mL). To the resulting slurry was added sodium sulfate (100 g) and the stirring was continued for an additional hour. The batch was clarified through a celite coated sparkler filter, and the filter cake was washed with MtBE, and the wash was added to the filtered batch. The filtrate was concentrated under reduced pressure using a rotary evaporator until the light solvents stopped distilling. The remaining organic residue was wiped film distilled in two temperature stages (first pass: 160° C. at 15 mTorr vacuum then second pass: 170° C. at 15 mTorr vacuum) to afford 766 g (90% yield when corrected for the assay of the starting material) of $\Delta^9$-THC as a clear to light yellow viscous oil. The HPLC analysis of this product was comparable to the assay of earlier batches.

Example 4. Preparation of $\Delta^9$-THC from CBD Distillate, with Aqueous KF Workup CBD Distillate (500 g @85% CBD content) was dissolved in dichloromethane (2 liters) in a nitrogen inerted, 22 L glass reactor with an overhead stirrer, pressure equalizing addition funnel and a water-cooled reflux condenser to create a homogenized mixture. The reactor was inerted with nitrogen and triisobutylaluminum (200 mL of 1 M solution in hexane, 10 mol % catalyst) was then slowly added over 2 hours at a batch temperature between 18 and 30° C. The reaction mixture was stirred for approximately 6 hours at a temperature of 20 to 25° C., at which point the reaction was determined to be complete by TLC and HPLC analysis (<2.0% CBD by HPLC). The reaction was quenched with a mixture of potassium fluoride (28 g) in water (15 mL) and when the active catalyst was quenched, the reaction mixture was rotary evaporated under reduced pressure to ca. 0.5 L volume. The batch was diluted with methyl tert-butyl ether (MtBE) (2 L) and the mixture was stirred. To the stirred solution was added silica gel (30 g) and the stirring was continued for an additional hour. The batch was clarified through a celite coated sparkler filter, and the filter cake was washed with MtBE, and the wash was added to the filtered batch. The filtrate was concentrated under reduced pressure using a rotary evaporator until the light solvents stopped distilling. The remaining organic residue was short path distilled and the main fraction was collected at 165° C. to 175° C. at 25 mTorr vacuum to afford 228 g (80% yield when corrected for the assay of the starting material) of $\Delta^9$-THC as a clear to light yellow viscous oil. The HPLC analysis of this product was comparable to the assay of earlier batches.

Example 5. Preparation of $\Delta^9$-THC from CBD Distillate, with Aqueous Workup CBD Distillate (15 kg @85% CBD content) was dissolved in dichloromethane (75 liters) in a nitrogen inerted, 150 L cylindrical glass reactor with an overhead stirrer, pressure equalizing addition funnel and a water-cooled reflux condenser to create a homogenized mixture. The reactor was inerted with nitrogen and triisobutylaluminum (6 L of 1 M solution in hexane, 10 mol % catalyst) was then slowly added over 2 hours at a batch temperature of 26° C. The reaction mixture was stirred for 6 hours at a temperature of 26 to 30° C., at which point the reaction was determined to be complete by TLC and HPLC analysis (<2.0% CBD by HPLC). The reaction was quenched by pumping the batch into a 200 L reactor equipped with a bottom valve and mechanical stirrer containing water (40 L) The addition time was about 30 minutes. The biphasic mixture was stirred for an additional 2 hours. The stirring was stopped, and the layers were separated. The bottom organic layer was saved for further processing and the remaining aqueous layer was extracted fresh dichloromethane (20 L) and this wash was added to the quenched organic solution. This solution was clarified through celite coated sparkler filter. The reactor and celite cake were rinsed with dichloromethane (5 L) and rinse was added to the clarified batch. The organic layer was concentrated under reduced pressure. The remaining organic residue was wiped film distilled (165° C. at 15 mTorr vacuum) to afford 8.7 kg (58% yield when corrected for the assay of the starting material) of $\Delta^9$-THC as a clear to light yellow viscous oil. The HPLC analysis of this product was comparable to the assay of earlier batches.

Example 6. Preparation of $\Delta^9$-THC from CBD Distillate Fortified with Kief, with the Aqueous Workup CBD Distillate (15 kg @85% CBD content) was dissolved in dichloromethane (75 liters) in a nitrogen inerted, 150 L cylindrical glass reactor with an overhead stirrer, pressure equalizing addition funnel and a water-cooled reflux condenser to create a homogenized mixture. To this solution was added Kief (30 g, 0.2 weight %) and the mixture was stirred until the Kief dissolved. The reactor was re-inerted with nitrogen and triisobutylaluminum (4 L of 1 M solution in hexane, 6.6 mol % catalyst) was then slowly added over 2 hours at a batch temperature of 26° C. The reaction mixture was stirred for 8 hours at a temperature of 26 to 30° C., at which point the reaction was determined to be complete by TLC and HPLC analysis (<2.0% CBD by HPLC). The reaction was quenched by pumping the batch into a 200 L reactor equipped with a bottom valve and mechanical stirrer containing water (40 L). The addition time was about 30 minutes. The biphasic mixture was stirred for an additional 2 hours and celite (3.0 kg) was added. This mixture was clarified through celite coated sparkler filter. The quench reactor and celite cake were rinsed with dichloromethane (5 L) and rinse was added to the clarified biphasic mixture. The stirring was stopped, and the layers were separated. The bottom organic layer was saved for further processing and the remaining aqueous layer was extracted fresh dichloromethane (20 L) and this wash was added to the quenched organic solution. The organic solution was concentrated under reduced pressure. The remaining organic residue was wiped film distilled (165° C. at 15 mTorr vacuum) to afford 13.1 kg (87.3% yield when corrected for the assay of the starting material) of $\Delta^9$-THC as a clear to light yellow viscous oil. The HPLC analysis of this product was comparable to the assay of earlier batches.

The following examples show $\Delta^9$-THC from CBD isolate.

Example 7. Preparation of $\Delta^9$-THC from CBD Isolate, Using Basic Ionic Resin Workup CBD Isolate (185 g at >95% purity) was dissolved in dichloromethane (1 L) in an argon inerted, 5 L, 3-necked round bottom flask with an overhead stirrer, pressure equalizing addition funnel and a water-cooled condenser. Triisobutylaluminum (60 mL of 1 M solution in hexane, 10 mol % catalyst) was then slowly added over 30 minutes at about room temperature. The reaction mixture was stirred for approximately 20 hours, until the reaction was complete by TLC and HPLC analysis (<2.0% CBD by HPLC). The reaction was quenched with water (1 L) and the biphasic mixture was stirred for about 1 hour. The biphasic mixture was passed through a water washed Amberlyst A21 (mildly basic) column The biphasic reaction mixture was then clarified through a celite loaded sparkler filter. The celite cake and reaction vessels were rinsed with dichloromethane (1 L) and combined with the clarified biphasic batch mixtures. The layers were separated, and the water layer was washed with fresh dichloromethane (250 mL) The combined organic layers were transferred to a short path distillation apparatus and concentrated under reduced pressure and the residue was distilled (170° C. at 15 mTorr vacuum) to afford 135 g; (73% yield) of $\Delta^9$-THC as a clear to light yellow viscous oil. The HPLC analysis of this product showed 93% $\Delta^9$-THC and 4% unreacted CBD.

TABLE—Quantitative Results
Quantitative Results

| | Detector A | | |
|---|---|---|---|
| ID# | Name | Ret. Time | Dry weight % |
| 1 | CBDV | — | 0.00 |
| 2 | CBDA | — | 0.00 |
| 3 | CBGA | — | 0.00 |
| 4 | CBG | — | 0.00 |
| 5 | CBD | 4.080 | 4.12 |
| 6 | THCV | — | 0.00 |
| 7 | CBN | — | 0.00 |
| 8 | Δ9-THC | 6.586 | 92.92 |
| 9 | Δ8-THC | — | 0.00 |
| 10 | CBC | — | 0.00 |
| 11 | THCA | — | 0.00 |

Example 8. Scale Up Preparation of $\Delta^9$-THC from CBD Isolate, Using Basic Ionic Resin Workup CBD Isolate (15 kg at >95% purity) was dissolved in dichloromethane (75 liters) in a nitrogen inerted, 150 L, cylindrical glass reactor with an overhead stirrer, pressure equalizing addition funnel and a water-cooled reflux condenser. to create a homogenized mixture. Triisobutylaluminum (3 L of 1 M solution in hexane, 10 mol % catalyst) was then slowly added over 30 minutes maintaining the reactor below 25° C. The reaction mixture was stirred for approximately 20 hours at which point the reaction was determined to be complete by TLC and HPLC analysis (<2.0% CBD by HPLC). The solution was quenched with water (25 L) and stirred for 1 hour, then circulated through a pair of water washed Amberlyst A21 resin column for two hours. The reaction mixture was then filtered through a celite loaded sparkler filter. The celite cake and reaction vessels were rinsed with dichloromethane (5 L) and combined with the total mixtures of solvents. The layers were separated, and the aqueous layer was washed with fresh dichloromethane (2.5 L) and the remaining aqueous layer was disposed. The organic solvent containing the desired product was concentrated under reduced pressure and the residue was wiped film distilled (165° C. at 15 mTorr vacuum) to afford 10.2 kg (68% yield) of $\Delta^9$-THC as a clear to light yellow viscous oil. The HPLC analysis of this product showed 93% $\Delta^9$-THC and 4% unreacted CBD.

Example 9. Preparation of $\Delta^9$-THC from CBD Isolate Fortified with Kief, with the Aqueous Workup CBD Isolate (300 g at >98% purity) was dissolved in dichloromethane (2 L) in an argon inerted, 12 L, 3-necked round bottom flask with an overhead stirrer, pressure equalizing addition funnel and a water-cooled condenser. To this solution was added Kief (3 g, 1 weight %) and the mixture was stirred until the Kief dissolved. Triisobutylaluminum (100 mL of 1 M solution in hexane, 10 mol % catalyst) was then slowly added over 30 minutes at about room temperature. The reaction mixture was stirred for approximately 20 hours, until the reaction was complete by TLC and HPLC analysis (<2.0% CBD by HPLC). The reaction was quenched with water (1 L) and the biphasic mixture was stirred for about 1 hour. Celite (66 g) was added to the batch and the slurry was stirred for 1 hour. The reaction mixture was then clarified through a celite loaded sparkler filter. The celite cake were rinsed with dichloromethane (1 L) and combined with the clarified biphasic mixtures. The layers were separated, and the water layer was washed with fresh dichloromethane (250 mL) The combined organic layers were transferred to a short path distillation apparatus and concentrated under reduced pressure and the residue was distilled (170° C. at 15 mTorr vacuum) to afford 235 g; (78% yield) of $\Delta^9$-THC as a clear to a pale-yellow viscous oil. The HPLC analysis of this product showed 93% A9-THC and 4% unreacted CBD.

The following examples demonstrate $\Delta^9$-THC from combined CBD distillate and isolate.

Example 10. Preparation of $\Delta^9$-THC from Combined CBD Distillate and Isolate, with Aqueous Workup CBD Distillate (7.5 kg @85% CBD content) and CBD isolate (7.5 kg at >95% purity) are dissolved in dichloromethane (75 liters) in a nitrogen inerted, 150 L cylindrical glass reactor with an overhead stirrer, pressure equalizing addition funnel and a water-cooled reflux condenser to create a homogenized mixture. The reactor is inerted with nitrogen and triisobutylaluminum (6 L of 1 M solution in hexane, 10 mol % catalyst) is then slowly added over 2 hours at a batch temperature of 26° C. The reaction mixture is stirred for 6 hours at a temperature of 26 to 30° C., at which point the reaction is determined to be complete by TLC and HPLC analysis (<2.0% CBD by HPLC). The reaction is quenched by pumping the batch into a 200 L reactor equipped with a bottom valve and mechanical stirrer containing water (40 L) The addition time is about 30 minutes. The biphasic mixture is stirred for an additional 2 hours. The stirring is stopped, and the layers are separated. The bottom organic layer is saved for further processing and the remaining aqueous layer is extracted fresh dichloromethane (20 L) and this wash is added to the quenched organic solution. This solution is clarified through celite coated sparkler filter. The reactor and celite cake are rinsed with dichloromethane (5 L) and rinse is added to the clarified batch. The organic layer is concentrated under reduced pressure. The remaining organic residue is wiped film distilled (165° C. at 15 mTorr vacuum) to afford 8.7 kg (58% yield when corrected for the assay of the starting material) of $\Delta^9$-THC as a clear to light yellow viscous oil. The HPLC analysis of this product is comparable to the assay of earlier batches.

Example 11. Preparation of $\Delta^9$-THC from CBD Distillate and Isolate Fortified with Kief, with the Aqueous Workup CBD Distillate (7.5 kg @85% CBD content) and CBD isolate (7.5 kg at >95% purity) are dissolved in dichloromethane (75 liters) in a nitrogen inerted, 150 L cylindrical glass reactor with an overhead stirrer, pressure equalizing addition funnel and a water-cooled reflux condenser to create a homogenized mixture. To this solution is added Kief (30 g, 0.2 weight %) and the mixture is stirred until the Kief is dissolved. The reactor is re-inerted with nitrogen and triisobutylaluminum (4 L of 1 M solution in hexane, 6.6 mol % catalyst) is then slowly added over 2 hours at a batch temperature of 26° C. The reaction mixture is stirred for 8 hours at a temperature of 26 to 30° C., at which point the reaction is determined to be complete by TLC and HPLC analysis (<2.0% CBD by HPLC). The reaction is quenched by pumping the batch into a 200 L reactor equipped with a bottom valve and mechanical stirrer containing water (40 L). The addition time is about 30 minutes. The biphasic mixture is stirred for an additional 2 hours and celite (3.0 kg) is added. This mixture is clarified through celite coated sparkler filter. The quench reactor and celite cake are rinsed with dichloromethane (5 L) and rinse is added to the clarified biphasic mixture. The stirring is stopped, and the layers are separated. The bottom organic layer is saved for further processing and the remaining aqueous layer is extracted fresh dichloromethane (20 L) and this wash is added to the quenched organic solution. The organic solution is concentrated under reduced pressure. The remaining organic residue is wiped film distilled (165° C. at 15 mTorr vacuum) to afford 13.1 kg (87.3% yield when corrected for the assay of the starting material) of $\Delta^9$-THC as a clear to light yellow viscous oil. The HPLC analysis of this product is comparable to the assay of earlier batches.

Pharmaceutical Compositions/Medicaments

The compositions of the invention may be converted using customary methods into pharmaceutical compositions and medicaments. The pharmaceutical composition and medicaments contain the composition of the invention either alone or together with other active substances. Such pharmaceutical compositions and medicaments can be for oral, topical, rectal, parenteral, local, or inhalant use. They are therefore in solid or semisolid form, for example a $\Delta^9$-THC solution in sesame oil, a $\Delta^9$-THC composition in a liquifilm gelcap, or a color gelcap stable in light, or a 5 mg liquifilm gelcap, or a dosage form for delivery of $\Delta^9$-THC composition at 2.5 mg-40 mg or 5 mg-100 mg/day, oils, drops, lotions, balm, pills, tablets, creams, gelatin capsules, capsules, suppositories, soft gelatin capsules, gels, foams, powders, and formulated for internal use. For parenteral uses, those forms for intramuscular or subcutaneous administration can be used, or forms for infusion or intravenous injection can be used, and can therefore be prepared as solutions of the compositions and medicaments or as powders of the active compositions to be mixed with one or more pharmaceutically acceptable excipients or diluents, suitable for the aforesaid uses and with an osmolarity that is compatible with the physiological fluids. For local use, those preparations in the form of creams or ointments for topical use or in the form of sprays may be considered; for inhalant uses, preparations in the form of sprays, for example nose sprays, may be considered. Preferably, the composition and medicaments are administered topically or orally.

The pharmaceutical compositions and medicaments can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Nack Publishing Company, Easton, Pa., USA 1985).

On this basis, the pharmaceutical compositions and medicaments include, albeit not exclusively, the composition of the invention in association with one or more pharmaceutically acceptable vehicles or diluents, and are contained in buffered solutions with a suitable pH and iso-osmotic with the physiological fluids.

The compositions and medicaments are indicated as therapeutic agents either alone or in conjunction with other therapeutic agents or other forms of treatment. For example, in the case of skin care or cosmetic use, or for nausea, anxiety, stress, chronic pain, acute pain and used as an appetite stimulant. The compositions and agents of the invention are intended for administration to humans or animals.

In another embodiment, the invention provides for an edible product comprising a composition of the present invention. Edible products include a pure $\Delta^9$-THC oil formulated in a food composition selected from an edible, a meltable form for adding to hot beverages selected from coffee, tea, cider, cocoa, and mixed hot drinks, a powder or dissolvable form for adding to cold or room temperature beverages selected from water, tea, coffee, a soda/carbonate drink, a cider, a juice, an energy drink, beer, ale, wine, a liquor, a mixed beverage, a gummy, lozenge, a candy, a hard candy, a boiled sweets, lollipop, gummy candy, candy bar, chocolate, a brownie, a cookie, a trail bar, a cracker, a dissolving strip, a mint, a pastry, a bread, and a chewing gum.

Dosages

Dosages for $\Delta^9$-THC contemplated as within the scope of the invention include, without limitation, the following dosage examples:

1 mg to 2.5 mg THC edibles—for mild relief of symptoms like pain, stress, and anxiety; increased focus and creativity.

2.5 mg to 15 mg THC edibles—for stronger relief of pain and anxiety symptoms; sleep aid.

30 mg to 100 mg THC edibles—for patients living with inflammatory disorders, cancer, and other serious conditions.

Other preferred dosages of the invention include 1 mg, 2.5 mg, 5 mg, and 10 mg capsules. For chemotherapy, as a non-limiting example, a 5 mg capsule is taken 1-3 hours before chemotherapy, and then additional 5 mg capsules every 2-4 hours as prescribed or as necessary. For anxiety, appetite increase (e.g. in people diagnosed with AIDS), opioid withdrawal, or narcotic relapse prevention, a patient may take a 1 or 2 mg tablet twice per day, as prescribed.

In another embodiment, the $\Delta^9$-THC is co-administered with CBD as a combination delivered simultaneously, or as a combination delivered sequentially. A preferred embodiment includes a ratio of $\Delta^9$-THC to CBD of about 1:2, or 1:3, or 1:4, or 1:5.

Example 12. Oral Formulation

A >95% pure $\Delta^9$-THC oil is prepared, the $\Delta^9$-THC oil at a dosage of 1-500 mg/dose is homogenized with a dietary oil, an optional secondary solvent and/or surfactant at 0.1-10% w/v, and an optional antioxidant. An optional sweetener or flavorant may be added. An oral formulation of pure $\Delta^9$-THC is obtained. The dietary oil may comprise medium chain ($C_8$-$C_{12}$) and long chain ($C_{10}$-$C_{22}$) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with mid-chain triglycerides or long-chain triglycerides, sesame oil, vitamin E, soybean oil, vegetable oil, corn oil, olive oil, peanut oil, coconut oil, palmseed oil, and mixtures thereof. The optional secondary solvents are selected from ethanol, glycerol, propylene glycol, and polyethylene glycols.

Example 13. Oral Formulation

A >95% pure $\Delta^9$-THC oil is prepared, the $\Delta^9$-THC oil at a dosage of 1-500 mg/dose is formulated into a tincture, a gummi, or fast melt tab, by mixing a dietary wax, an optional secondary dietary oil, an optional secondary solvent and/or surfactant at 0.1-10% w/v, and an optional antioxidant. An optional sweetener or flavorant may be added. An oral formulation of pure $\Delta^9$-THC is obtained. The dietary wax may comprise beeswax, plant waxes, very long chain fatty acid waxes, and mixtures thereof. The dietary oil may comprise medium chain ($C_8$-$C_{12}$) and long chain ($C_{10}$-$C_{22}$) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from a very long chain fatty alcohol ($C_{24}$-$C_{34}$), ethanol, glycerol, propylene glycol, and polyethylene glycols.

Example 14. Oral Formulation

A >99% pure $\Delta^9$-THC oil is prepared, the $\Delta^9$-THC oil at a dosage of 1-500 mg/dose is formulated into a tincture, a gummi, or fast melt tab, by mixing with sesame oil and ethanol. An oral formulation of pure $\Delta^9$-THC is obtained.

Example 15. Oral Formulation

A 90-99% pure $\Delta^9$-THC oil is prepared, the $\Delta^9$-THC oil at a dosage of 1-500 mg/dose is formulated into a food composition selected from an edible, a meltable form for adding to hot beverages selected from coffee, tea, cider, cocoa, and mixed hot drinks, a powder or dissolvable form for adding to cold or room temperature beverages selected from water, iced tea, iced coffee, a soda/carbonate drink, a cider, a juice, an energy drink, beer, ale, wine, a fermented beverage such as Kombucha and Kefir, a liquor, a mixed beverage, a gummy, a lozenge, a candy, a hard candy, a boiled sweets, lollipop, gummy candy, candy bar, chocolate, a brownie, a cookie, a trail bar, a cracker, a dissolving strip, a mint, a pastry, a bread, and a chewing gum.

Topical Formulations

In preferred embodiments, the present compositions can additionally comprise at least one skin conditioning agent. In this regard, the present compositions preferably contain about 1% to about 15% by weight, and more preferably from about 5% to about 10% of at least one agent. The skin conditioning agent can help provide the softening, smoothing, lubricating, and skin conditioning features of the presently preferred compositions.

Preferred non-limiting examples of skin conditioning agents useful in the present compositions include petrolatum, red petrolatum, white petrolatum, liquid petrolatum, semi-solid petrolatum, light mineral oil, heavy mineral oil, white mineral oil, mineral oil alcohols, calamine, derivatives thereof, and mixtures thereof.

Organosiloxane

The presently preferred compositions can further comprise at least one organosiloxane. Organosiloxanes useful in the present compositions can be volatile or nonvolatile, including but not limited to polyalkylsilicones, cyclic polyalkylsiloxanes, polydialkylsiloxanes, polydiarylsiloxanes, polyalkarylsiloxanes, or cyclomethicones. Preferred polyalkylsiloxanes useful in this regard have a viscosity of from about 0.5 to about 100,000 centistokes at 25° C., and more preferably have a viscosity of less than 500 centistokes at 25° C.

Aqueous Solvent

The present compositions additionally comprise an aqueous solvent. Preferably the aqueous solvent is present in the instant compositions from about 50% to about 95% by weight, and more preferably from about 60% to about 90% by weight.

Emollient

Certain of the presently preferred compositions can additionally comprise at least one emollient. The present compositions may contain about 0.01% to about 5% by weight, and more preferably from about 0.1% to about 1% by weight of an emollient.

Dermatologically Acceptable Excipients

The preferred compositions discussed herein can additionally comprise at least one dermatologically acceptable excipient commonly known to those of ordinary skill in the art as useful in topical compositions. Preferred, non-limiting examples of dermatologically acceptable excipients useful in these compositions are those selected from the group consisting of moisturizers, preservatives, gelling agents, colorants or pigments, antioxidants, radical scavengers, emulsifiers, pH modifiers, chelating agents, penetration enhancers, derivatives thereof, and mixtures thereof.

Moisturizers

The presently preferred compositions may optionally further contain at least one moisturizer. Preferably, the presently preferred compositions can comprise about 0.01% to about 10% by weight of at least one moisturizer. Preferred non-limiting examples of moisturizers that can optionally be included in these compositions include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, hexylene glycol, propylene glycol, dipropylene glycol, sorbitol, derivatives thereof, and mixtures thereof.

Preservatives

The presently preferred compositions may optionally further contain at least one preservative. Preferred non-limiting examples of preservatives that can optionally be included in these compositions include benzyl alcohol, methyl paraben, ethyl paraben, derivatives thereof, and mixtures thereof. A particularly preferred preservative in this regard is benzyl alcohol or a derivative thereof. Additionally, the preservative is preferably present in an amount of about 0.1% to about 2.5% by weight of the overall weight of the composition.

Gelling Agents

The presently preferred compositions may optionally further contain a gelling agent. Preferred non-limiting examples of gelling agents that can optionally be included in these compositions include various cellulose agents, such as cellulosic polymers, methylcellulose, hydroxyethylcellulose, hydroxypropylcellulose, and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof. Exemplary polymers which may be useful in the preferred compositions in this regard include carboxy vinyl polymers, such as carboxypolymethylene. Additionally preferred gelling agents include Carbopol® and Carbomer® polymers (i.e. polyacrylic polymers) such as is available from Noveon Inc., Cleveland, Ohio. The gelling agent is preferably present in the instant compositions in an amount of from about 0.01% to about 10%, more preferably from about 0.1% to about 5%, and most preferably from about 0.1% to about 2%, by weight.

Antioxidants

The presently preferred compositions may optionally further contain at least one antioxidant. Preferably, the presently preferred compositions can comprise about 0.1% to about 5% by weight of at least one antioxidant. Preferred non-limiting examples of antioxidants that can optionally be included in these compositions include ascorbic acid, ascorbyl esters of fatty acids, magnesium ascorbyl phosphate, sodium ascorbyl phosphate, ascorbyl sorbate, tocopherol, tocopherol sorbate, tocopherol acetate, butylated hydroxy benzoic acid, thioglycolates, persulfate salts, 6-hydroxy-2,5,7,8-tetramethylchroman-2-carboxylic acid, lipoic acid, gallic acid, propyl gallate, uric acid, sorbic acid, lipoic acid, amines, N,N-diethylhydroxylamine, N-acetyl-L-cysteine, amino-guanidine, sulfhydryl compounds, glutathione, dihydroxy fumaric acid, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, rosemary extracts, derivatives thereof, and mixtures thereof.

Emulsifiers

The presently preferred compositions may optionally further contain an emulsifier. Preferably, the presently preferred compositions can comprise about 0.05% to about 15% by weight, and more preferably from about 0.5% to about 10% by weight of at least one emulsifier. Preferred, non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-8 stearate, PEG-100 stearate, derivatives thereof, and mixtures thereof.

pH Modifiers

The presently preferred compositions may optionally further contain a pH modifier. Preferably, the presently preferred compositions can comprise about 0.001% to about 1% by weight of a pH modifier. Preferred non-limiting examples of neutralizing pH modifiers that can optionally be included in these compositions include inorganic hydroxides, inorganic oxides, inorganic salts of weak acids, derivatives thereof, and mixtures thereof. Preferred, non-limiting examples of inorganic hydroxides useful in this regard include ammonium hydroxide, alkali metal hydroxide, alkaline earth metal hydroxides, derivatives thereof, and mixtures thereof. Preferred inorganic hydroxides useful in this regard include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof. Preferred, non-limiting examples of inorganic oxides useful in this regard include magnesium oxide, calcium oxide, derivatives thereof, and mixtures thereof. Preferred, non-limiting examples of inorganic salts of weak acids useful in this regard include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

Chelating Agents

The presently preferred compositions may optionally further contain a chelating agent. Preferably, the presently preferred compositions can comprise about 0.01% to about 1% by weight of a chelating agent. Preferred non-limiting examples of chelating agents that can optionally be included in these compositions include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and mixtures thereof.

In addition to those enumerated above, any other pharmaceutically active agent, occlusive skin conditioning agent, emollient, penetration enhancer, organosiloxane, moisturizer, preservative, gelling agent, colorant or pigment, antioxidant, radical scavenger, emulsifier, pH modifier, chelating agent, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as Goodman and Gillman's The Pharmacological Bases of Therapeutics, 8th Ed., Gilman et al. Eds. Pergamon Press (1990) and Remington's Pharmaceutical Sciences, 17th Ed., Mack Publishing Co., Easton, Pa. (1990), both of which are incorporated by reference herein in their entirety.

In another particularly preferred embodiment, the presently preferred pharmaceutical compositions are formulated in a lotion, cream, ointment, gel, suspension, emulsion, foam, aerosol, or other pharmaceutically acceptable topical dosage form.

Example 16. Topical Transdermal Composition

A >90% pure $\Delta^9$-THC oil is prepared, the $\Delta^9$-THC oil at a dosage of 1-500 mg/dose is formulated into a transdermal formulation by mixing pure $\Delta^9$-THC with a transdermal formulation base, the transdermal formulation base comprising an emulsion formed from an aqueous phase and an oil phase, and an penetration enhancer, an optional emulsifier, and an optional emollient. A topical transdermal $\Delta^9$-THC composition is thereby obtained.

Example 17. Topical Composition

A >95% pure $\Delta^9$-THC oil is prepared, the $\Delta^9$-THC oil at a dosage of 1-500 mg/dose is formulated as a cream, an ointment, foam, gel, lotion, ointment, paste, spray, or solution. A topical >95% pure $\Delta^9$-THC composition is thereby obtained. The cream or ointment is a water-in-oil or oil-in-water emulsion containing less than 20% water, greater than 50% hydrocarbons, waxes and/or polyols, and using a surfactant to create a semi-solid, spreadable composition. The foam is a cream or ointment packaged in a pressurized container and delivered with a gas.

Example 18. Topical Composition

A >99% pure $\Delta^9$-THC oil is prepared, the $\Delta^9$-THC oil at a dosage of 1-500 mg/dose is formulated as a topical composition comprising: (i) >99% pure $\Delta^9$-THC oil, and (ii) a carrier formulation comprising: a self-emulsifying wax (i.e. glyceryl stearate, PEG-100 stearate), a polyol (glycerin), a fatty alcohol (cetyl alcohol), a moisturizer (allantoin), a hydrocarbon moisturizer/occlusive (petrolatum), an emulsifier (i.e. steareth-21), an antioxidant (tocopheryl acetate), and optionally a fragrance, a stabilizer (xanthan gum), a skin conditioner (i.e dipotassium glycyrrhizate), Aloe Barbadensis Leaf Juice, a surfactant (triethanolamine), an anti-inflammatory (i.e. bisabolol), and a preservative (disodium EDTA).

Any of the topical formulations herein may include a hydrocarbon base ("oleaginous"), such a white petrolatum or white ointment, an absorption base (water-in-oil) such as hydrophilic petrolatum or lanolin, water-removable base (oil-in-water) such as hydrophilic ointment, or a water-soluble base, such as polyethylene glycol ointment.

The topical formulation may also include a wax such as beeswax, plant waxes, very long chain fatty acid waxes, and mixtures thereof, an oil such as medium chain ($C_8$-$C_{12}$) and long chain ($C_{10}$-$C_{22}$) triglycerides, and alone or in combination with MCT or LCT, sesame oil, vitamin E, soybean oil, vegetable oil, corn oil, olive oil, peanut oil, coconut oil, palmseed oil, and mixtures thereof. Any of the topical formulations herein may include solvents are selected from a very long chain fatty alcohol ($C_{24}$-$C_{34}$), ethanol, glycerol, propylene glycol, and polyethylene glycols. Any of the topical formulations herein may include a penetration enhancer such as ethoxydiglycol (i.e. transcutanol) or an equivalent.

Uses

As used herein, the terms "administering", "administration", and like terms refer to any method which, in sound medical or cosmetic practice, delivers the composition to a subject in such a manner as to provide a positive effect on a dermatological disorder, condition, or appearance. The compositions are preferably administered such that they cover the entire area to be treated. "Direct administration" refers to any method which, in sound medical or cosmetic practice, delivers the composition to a subject without the use of another composition, delivery agent, or device. "Indirect administration" refers to any method which, in sound medical or cosmetic practice, delivers the composition to a subject with the use of at least one other composition, delivery agent, or device.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a positive effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

Anti-Tampering and Anti-Counterfeiting

The invention also includes adding a signature marker molecule to a product containing the high purity $\Delta^9$-THC oil made herein.

Example 19. Authentication, Anti-Counterfeit Markers

Step 1. A product containing the high purity $\Delta^9$-THC oil is prepared. The product can include an over-the-counter product or a pharmaceutical composition or medicament. The product or dosage form can include manufactured for oral, topical, rectal, parenteral, local, or inhalant use. The product may be in in solid or semisolid form, and may include oils, drops, sprays, lotions, balm, pills, tablets, creams, ointments, gelatin capsules, capsules, suppositories, soft gelatin capsules, gels, foams, powders, and formulations for internal use including intramuscular forms, subcutaneous forms, infusion forms, injectable forms, reconstitutable powder forms.

Step 2. A signature marker molecule is added to the product and/or the packaging. The signature molecule marker can be a single identifier or may be specific combination of chemicals. Where the signature marker molecule is a single identifier is used, the invention contemplates the use of a DNA molecular tag such as the SigNature® molecular tag (Applied DNA Sciences, Inc.), which is a DNA based identifier added as a film to oral or topical dosage forms to form a covert authentication platform. This DNA tag functions as a "molecular bar code", enabling identification to a source, as a product type, or other meaningful attribute. To validate the product, the product is tested for the presence of the tag using a rt-PCR kit that includes reagents and a reader, such as the reagent mix Sig-Nify® Reagent Mix and the SigNify® IF portable reader (Applied DNA Sciences, Inc.) which uses real-time polymerase chain reaction (rt-PCR).

Where a signature marker molecule is a specific combination chemicals, the invention contemplates the use of specific trackable batches that containing specific varying amounts and types of substitutable inactive agents. Such inactive agent combinations can include one or more of a solvent, surfactant, antioxidant, triglyceride, oil, conditioning agent, organosiloxane, emollient, excipient, moisturizer, preservative, gelling agent, emulsifier, pH modifier, chelator, colorant, visible pigment and/or non-visible pigment (UV or near IR) such as a fluorescent pigment. By selecting and tracking the specific amount and type of inactive agent, the product can be authenticated.

Figure 8:
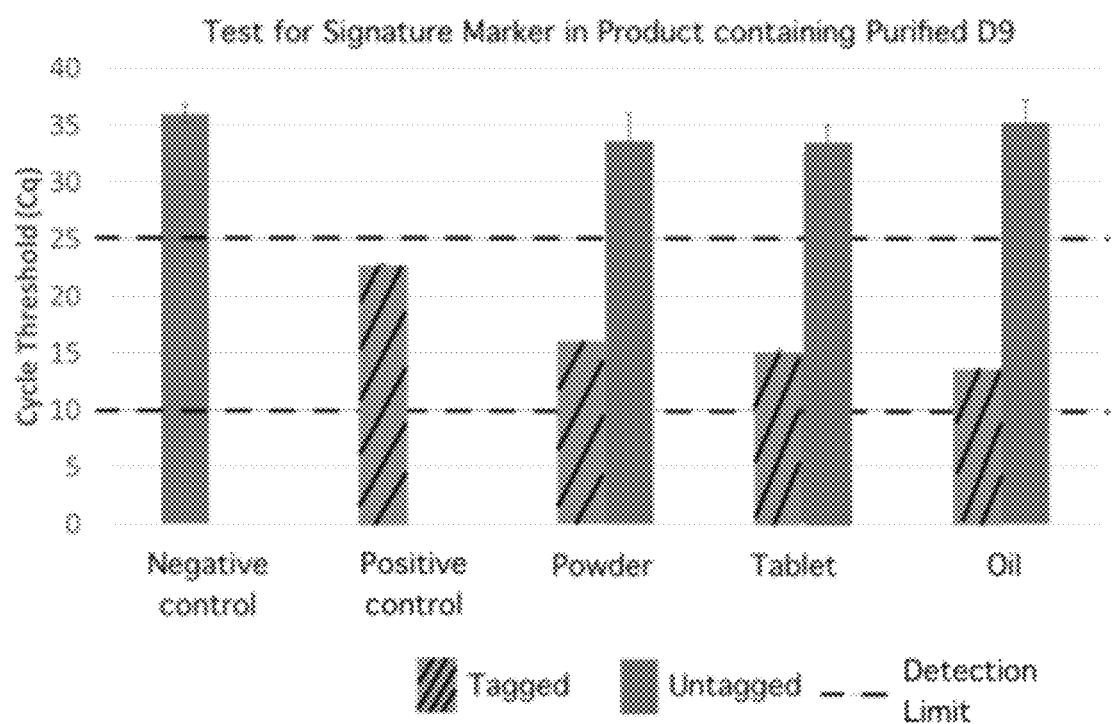
FIG. 8 is a bar graph of a prospective example showing the use of a signature marker to authenticate the high purity $\Delta^9$-tetrahydrocannabinol made according to the process herein.

Step 3. Testing products for authenticity includes where a product containing the signature marker molecule will be positively identified in authentic products, and products that do not contain the signature marker molecule can be identified as counterfeit products.

Where samples are analyzed by rt-PCR, the resulting cycle threshold (Cq) can be compared against negative and positive controls, as shown in FIG. 8. A higher Cq value indicates more cycle time to amplify DNA tag to threshold and therefore lower quantity of DNA. Any Cq value greater than 25 is considered non-detectable. The negative control and untagged product provided a Cq>30 indicating no detection of the tag. In comparison, the tagged product samples and positive control had Cq values of 10-25 confirming the presence of the tag.

Experimental Introduction:

Unless otherwise noted, reagents and solvents were used as received from commercial suppliers.

TLC analysis of $\Delta^9$-THC for in-process control: Analyses were obtained using MilliporeSigma TLC Silica Gel 60 F254 2.5×7.5 cm plates eluted with a 1:1 mixture of chloroform and 50% benzene and visualized in TLC chamber with UV 254 light.

Key Rf values: CBD 0.5, $\Delta^9$-THC 0.7 and $\Delta^8$-THC 0.8.

HPLC of $\Delta^9$-THC is a non-limiting preferred method for in-process control and product purity. In a specific, non-limiting example, the $\Delta^9$-THC purity was obtained using the following HPLC system. Analyses were obtained on a Shimadzu HPLC machine, Model LC 2030C-Plus using a Raptor ARC-18, 2.7 um, 150×4 6 mm column, at 35° C. column temperature, with a UV detector set at 220 nm and solvent gradient program:

TABLE

| HPLC | | | |
|---|---|---|---|
| Time (min) | Flow (mL/min) | % A | % B |
| 0.0 | 1.6 | 30.0 | 70.0 |
| 3.0 | 1.6 | 30.0 | 70.0 |
| 7.0 | 1.6 | 15.0 | 85.0 |
| 7.01 | 1.6 | 5.0 | 95.0 |
| 8.0 | 1.6 | 5.0 | 95.0 |
| 10.0 | 1.6 | 30.0 | 70.0 |

Figure 9:
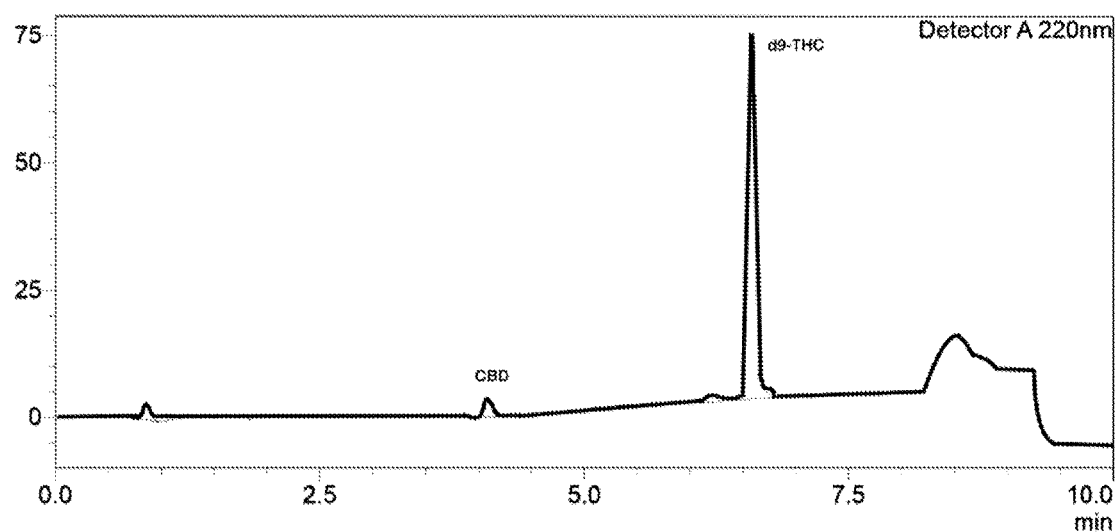
FIG. 9 is a chromatogram showing the HPLC results at 220 nm of a UV detector from 0.0-10.0 minutes of a CBD peak and a d9-THC peak.

Mobile Phase A=Water with 0.085% v/v Phosphoric acid
Mobile Phase B=Acetonitrile with 0.085% Phosphoric acid
Total Run Time: 10 min Referring now to FIG. 9, FIG. 9 is a chromatogram showing the HPLC results at 220 nm of a UV detector from 0.0-10.0 minutes of a CBD peak and a d9-THC peak.

EQUIVALENTS

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed as the invention:

1. A process, comprising:
extracting CBD distillate or isolate from industrial hemp having less than 0.3% $\Delta$9-THC;
dissolving the CBD distillate or isolate in dichloromethane to create a homogenized mixture;
adding the homogenized mixture to a reactor vessel and adding a 10 mol % solution of organoaluminum catalyst in inert hydrocarbon solvent slowly over 30 minutes at a temperature of 18-30° C. to create a reaction mixture;
stirring the reaction mixture for approximately 6-20 hours at a temperature of −20° C. to about 70° C.;
quenching the reaction mixture with water or a C2-C4 alcohol, and stirring for 1 hour;
filtering the reaction mixture through a filter selected from diatomaceous earth, perlite, bentonite clay, celite, cellulose, or a mixture thereof, to collect a filtrate, and rinsing the filter and reaction vessel with a rinse solvent selected from dichloromethane, hexanes, or a combination of both, removing the water or a C2-C4 alcohol quench layer from the rinse, and combining the filtrate and the rinse to obtain a combined filtrate and rinse mixture;

performing a split path distillation of the combined filtrate and rinse mixture, wherein the split path distillation comprises vacuum distilling the combined filtrate and rinse mixture with a short path vacuum distillation system, wherein said vacuum distilling removes the rinse solvent and volatile cannabidiol impurities having a boiling point less than about 157° C. at about 15-20 mTorr vacuum to obtain Δ9-THC crude distillate, and then performing a vacuum wiped film distillation with a wiped film distillation unit at about 160° C. at about 15-20 mTorr vacuum to obtain a Δ9-THC oil comprising over about 90% Δ9-THC and about 4% or less of unreacted CBD, wherein said wiped film distilling removes high temperature cannabinoid impurities having a non-vacuum boiling higher than 160° C.

2. The process of claim 1,
wherein the extract from industrial hemp having less than 0.3% Δ9-THC is CBD distillate comprising at least 85% CBD and;
wherein the solvent is dichloromethane;
wherein the organoaluminum catalyst is triisobutylaluminum in inert hydrocarbon solvent (iBu3Al);
wherein quenching uses water;
wherein the filter is a diatomaceous earth filter;
wherein split path distillation comprises short path distillation first to concentrate the filtrate under reduced pressure to obtain a main portion separated from a heads portion and a tails portion, followed by wiped film distillation of the main portion; and,
wherein the Δ9-THC oil comprises 95% or greater Δ9-THC and 2% or less unreacted CBD.

3. The process of claim 1,
wherein the extract from industrial hemp having less than 0.3% Δ9-THC is CBD isolate;
wherein the solvent is dichloromethane;
wherein the organoaluminum catalyst is triisobutylaluminum (iBu3Al) in inert hydrocarbon solvent;
wherein quenching uses water;
wherein the filter is a diatomaceous earth filter;
wherein split path distillation comprises short path distillation first to concentrate the filtrate under reduced pressure to obtain a main portion separated from a heads portion and a tails portion, followed by wiped film distillation of the main portion; and,
wherein the Δ9-THC oil comprises 95% or greater Δ9-THC and 2% or less unreacted CBD.

4. The process of claim 1, wherein the CBD extract is about 85% CBD and 15% other cannabinoids, wherein the organoaluminum catalyst is 1-2 molar triisobutylaluminum in hexane, wherein the temperature of 25-30° C. to create a reaction mixture, and wherein the stirring is performed until CBD is 2-4% in the reaction mixture.

5. The process of claim 1, wherein the CBD extract is optically active chiral CBD having an R,R or trans(-) rotation.

6. The process according to claim 1, wherein the organoaluminum catalyst is selected from the group consisting of a trialkyl- or triarylaluminum, dialkyl- or diarylaluminum halide, alkylarylaluminum halide, dialkyl- or alkylaryl- or diarylaluminum alkoxide or aryloxide, dialkyl- or alkylaryl- or diarylaluminum thioalkoxide or thioarylate, dialkyl- or alkylaryl- or diarylaluminum carboxylate, alkyl- or arylaluminum dihalide, alkyl- or arylaluminum dialkoxide or diaryloxide or alkylaryloxide, alkyl- or arylaluminum dithioalkoxide or dithioarylate, alkyl- or arylaluminum dicarboxylate, aluminum trialkoxide or triaryloxide or mixed alkylaryloxide, aluminum triacylcarboxylate, and mixtures thereof.

7. The process according to claim 6, wherein the organoaluminum catalyst is a C1-C30 alkylaluminum-based catalyst.

8. The process according to claim 6, wherein the organoaluminum-based Lewis acid catalyst is ethyl aluminum dichloride, diethylaluminum chloride, diethylaluminum sesquichloride, isobutylaluminum dichloride, diisobutylaluminum chloride, or mixtures thereof.

9. The process according to claim 6, wherein the trialkylaluminum is trimethylaluminum, triethylaluminum, triisopropylaluminum, triisobutylaluminum, trioctylaluminum, or tridecylaluminum.

10. The process according to claim 6, wherein the trialkylaluminum is triisobutylaluminum (iBu3Al).

11. The process according to claim 6, wherein the trialkylaluminum is 1-2 molar triisobutylaluminum in hexane or 1 molar triisobutylaluminum in toluene.

12. The process according to claim 1, wherein the organoaluminum catalyst is in an amount of from about 0.5 mol % to about 100 mol % with respect to the homogenized mixture.

13. The process according to claim 1, wherein said organoaluminum catalyst in an amount of from about 5 mol % to about 15 mol % with respect to the homogenized mixture.

14. The process according to claim 1, comprising an additional aprotic solvent selected from toluene, hexane, heptane, xylene, dimethylformamide, dimethylsulfoxane, dichloromethane, or a mixture thereof.

15. The process according to claim 1, wherein the solvent is dichloromethane.

16. The process according to claim 1, wherein said stirring is carried out at a temperature of from about −20° C. to about 70° C.

17. The process according to claim 1, wherein said stirring is carried out at a temperature of from about −10° C. to about 70° C.

18. The process according to claim 1, wherein said stirring is carried out at a temperature of from about 0° C. to about 40° C.

19. The process according to claim 1, wherein said stirring is carried out at a temperature of from about 10° C. to about 35° C.

20. The process according to claim 1, comprising an additional purification method selected from the group consisting of chromatography, and countercurrent extraction.

21. The process according to claim 1, wherein the CBD distillate or isolate from industrial hemp having less than 0.3% Δ9-THC is combined with kief or a crude CBD extract before dissolving in dichloromethane to create a homogenized mixture.

22. The process of claim 1, wherein the homogenized mixture comprises a mixture of CBD distillate and CBD isolate.

23. The process of claim 1, wherein the homogenized mixture comprises a mixture of CBD distillate and CBD isolate and the homogenized mixture is combined with kief or a crude CBD extract.

24. A Δ9-THC oil, comprising at least 95% Δ9-THC, and 2-4% CBD.

25. The Δ9-THC oil of claim 24 formulated as a pharmaceutical composition as a tincture, a gummi, or fast melt tab comprising: (i) >95% pure Δ9-THC oil at a dosage of 1-500 mg/dose, and (ii) a pharmaceutically acceptable carrier comprising a dietary wax, an optional secondary dietary oil, an optional secondary solvent and/or surfactant at 0.1-10% w/v, and an optional antioxidant, and an optional sweetener or flavorant.

26. The Δ9-THC oil of claim 24 formulated as a pharmaceutical composition as a tincture, a gummi, or fast melt tab comprising: (i) >95% pure Δ9-THC oil at a dosage of 1-500 mg/dose, and (ii) a pharmaceutically acceptable carrier comprising: dietary wax selected from the group consisting of bees wax, plant waxes, very long chain fatty acid waxes, and mixtures thereof, a dietary oil selected from the group consisting of medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglycerides, medium chain triglycerides (MCT) or long chain triglycerides (LCT), sesame oil, vitamin E, soybean oil, vegetable oil, corn oil, olive oil, peanut oil, coconut oil, palmseed oil, and mixtures thereof, and an optional secondary solvents selected from the group consisting of a very long chain fatty alcohol (C24-C34), ethanol, glycerol, propylene glycol, and polyethylene glycols.

27. The Δ9-THC oil of claim 24, formulated as a topical formulation for skin care and cosmetic use, at a dosage of 1-500 mg/dose, said topical composition comprising: (i) >95% pure Δ9-THC oil, and (ii) a carrier formulation comprising: a self-emulsifying wax, a polyol, a fatty alcohol, a moisturizer, a hydrocarbon moisturizer/occlusive, an emulsifier, an antioxidant, and optionally a fragrance, a stabilizer, a skin conditioner, Aloe Barbadensis Leaf Juice, a surfactant, an anti-inflammatory, and a preservative.

28. The Δ9-THC oil of claim 24, formulated as a topical formulation for skin care and cosmetic use, at a dosage of 1-500 mg/dose, said topical composition comprising: (i) >95% pure Δ9-THC oil, and (ii) a carrier formulation comprising: a self-emulsifying wax comprising glyceryl stearate, and/or PEG-100 stearate, a polyol comprising glycerin, a fatty alcohol comprising cetyl alcohol, a moisturizer comprising allantoin, a hydrocarbon moisturizer/occlusive comprising petrolatum, an emulsifier comprising steareth-21, an antioxidant comprising tocopheryl acetate, and optionally a fragrance, a stabilizer comprising xanthan gum, a skin conditioner comprising dipotassium glycyrrhizate, Aloe Barbadensis Leaf Juice, a surfactant comprising triethanolamine, an anti-inflammatory comprising bisabolol, and a preservative comprising disodium EDTA.

29. The Δ9-THC oil of claim 24, formulated as a cream, an ointment, foam, gel, lotion, ointment, paste, spray, or solution, comprising: (i) >95% pure Δ9-THC, and a topical carrier selected from the group consisting of cream, ointment, foam, gel, lotion, ointment, paste, spray, and solution, wherein the cream, ointment, gel, lotion, ointment, paste is a water-in-oil or oil-in-water emulsion containing less than 20% water, greater than 50% hydrocarbons, waxes and/or polyols, and includes a surfactant to create a semi-solid, spreadable composition, wherein the foam is a cream or ointment packaged in a pressurized container and delivered with a gas, wherein the spray is a liquid packaged in a pressurized container and delivered with a gas, wherein the solution is a liquid packaged in a container and delivered with an alcohol.

30. The Δ9-THC oil of claim 24, formulated as a liquid-filled gelcap.

31. The Δ9-THC oil of claim 24, formulated in a food composition.

32. The Δ9-THC oil of claim 24, formulated in a food composition selected from an edible, a meltable form for adding to hot beverages selected from coffee, tea, cider, cocoa, and mixed hot drinks, a powder or dissolvable form for adding to cold or room temperature beverages selected from water, iced tea, iced coffee, a soda/carbonate drink, a cider, a juice, an energy drink, beer, ale, wine, a fermented beverage, a liquor, a mixed beverage, a gummy, a lozenge, a candy, a hard candy, a boiled sweets, lollipop, gummy candy, candy bar, chocolate, a brownie, a cookie, a trail bar, a cracker, a dissolving strip, a mint, a pastry, a bread, and a chewing gum.

\* \* \* \* \*